United States Patent [19]

Pilgrim et al.

[11] Patent Number: 4,732,912

[45] Date of Patent: Mar. 22, 1988

[54] PHENOL DERIVATIVES

[75] Inventors: William R. Pilgrim, Reims, France; Derek W. Young, Wilmslow, United Kingdom; Brian S. Tait; Graham C. Crawley, both of Macclesfield, United Kingdom; Philip N. Edwards, Bramhall, United Kingdom; George B. Hill, Sandbach, United Kingdom

[73] Assignee: Imperial Chemical Industries PLC, London, England

[21] Appl. No.: 604,964

[22] Filed: Apr. 27, 1984

[30] Foreign Application Priority Data

Apr. 28, 1983 [GB] United Kingdom ............... 8311678

[51] Int. Cl.$^4$ .................. A61K 31/10; A61K 31/215; A61K 31/275; C07C 147/10
[52] U.S. Cl. .................. 514/510; 514/708; 514/709; 514/710; 514/712; 514/713; 558/268; 558/269; 558/270; 558/273; 558/413; 558/414; 558/416; 558/423; 560/100; 560/108; 560/139; 568/29; 568/33; 568/36; 568/37; 568/47; 568/48; 568/49
[58] Field of Search .................. 568/33, 47, 37, 31, 568/27, 43, 42, 47, 49, 52, 29, 48, 36; 558/268, 270, 269, 273, 413, 414, 416, 423; 560/10, 100, 108, 139; 514/706, 708, 709, 710, 711, 510, 647, 657, 520, 522, 569, 618, 629, 681, 602, 512, 712, 713; 564/308, 162, 222, 85; 562/427, 428; 260/465 F, 463

[56] References Cited

U.S. PATENT DOCUMENTS

| 3,296,304 | 1/1967 | Tilley et al. ............... 260/558 |
| 3,506,716 | 4/1970 | Peterli et al. .............. 568/52 |
| 3,539,642 | 11/1970 | Pesterfield ............... 260/559 |
| 3,546,163 | 12/1970 | Peterli ..................... 568/52 |
| 3,729,443 | 4/1973 | Peterli ..................... 568/52 |
| 3,736,347 | 5/1973 | Billett et al. .............. 560/101 |
| 3,829,474 | 8/1974 | Billett et al. .............. 562/468 |
| 3,993,683 | 11/1976 | Nickl et al. ............... 568/37 |
| 4,055,539 | 10/1977 | Rosenberger .............. 568/47 |
| 4,136,197 | 1/1979 | Hubner ..................... 562/451 |
| 4,191,776 | 3/1980 | Nickl et al. ............... 568/37 |
| 4,304,940 | 12/1981 | Wedemeyer ................ 568/51 |

FOREIGN PATENT DOCUMENTS 1257266 12/1971 United Kingdom .

OTHER PUBLICATIONS

S. W. Landvatter et al, "Nonsteroidal Estrogens: Synthesis and Estrogen Receptor Binding Affinity of Derivatives of (3R*,4S*)-3,4-Bis(4-hydroxyphenyl)hexane (Hexestrol) and (2R*,3S*)-2,3-Bis(4-hydroxyphenyl)pentane (Norhexestrol) Functionalized on the Side Chain, J. Med. Chem., 1982, pp. 1300–1307.

Primary Examiner—Mary E. Ceperley
Attorney, Agent, or Firm—Cushman, Darby & Cushman

[57] ABSTRACT

A phenol derivative of the formula

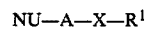

NU—A—X—R$^1$ wherein NU is a defined bis-phenolic nucleus including a hydroxyphenyl-hydroxynaphthyl; hydroxyphenyl-hydroxyindanyl, hydroxyphenyl-hydroxybenzothienyl or di-hydroxyphenyl-ethylene or vinylene nucleus; wherein A is alkylene, alkenylene or alkynylene which may be interrupted by phenylene or other linkages,
wherein R$^1$ is hydrogen, or alkyl, alkenyl, cycloalkyl, halogenoalkyl, aryl or arylalkyl, or R$^1$ is joined to R$^2$, and wherein X is —CONR$^2$—, —CSNR$^2$—, —NR$^{12}$CO—, —NR$^{12}$CS—, —NR$^{12}$CONR$^2$—,

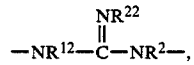

$$-NR^{12}-\overset{\overset{NR^{22}}{\|}}{C}-NR^2-,$$

—SO$_2$NR$^2$— or —CO—, or, when R$^1$ is not hydrogen, is —NR$^{12}$COO—, —S—, —SO— or —SO$_2$—,
wherein R$^2$ is hydrogen or alkyl, or R$^1$ and R$^2$ together form alkylene;
wherein R$^{12}$ is hydrogen or alkyl, and wherein R$^{22}$ is hydrogen, cyano or nitro;
or a salt thereof when appropriate. The compounds possess antioestrogenic activity and may be used for the treatment of hormone-dependent breast tumours or of anovulatory infertility.

9 Claims, No Drawings

PHENOL DERIVATIVES

This invention relates to new phenol derivatives which possess antioestrogenic activity.

Various antioestrogens are now known. Two such compounds, tamoxifen and clomiphene, are commercially available, and others, for example nafoxidine, trioxifene and a number of compounds with code-numbers such as Cl 628 and LY 117018, have been the subject of clinical trials. Many oestrogenic compounds are also known, and in particular oestrogens based on hexoestrol bearing an amidic function, of the general formula:

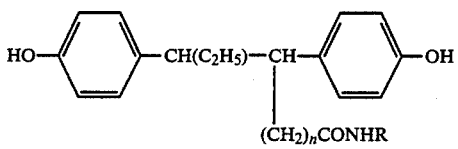

$(CH_2)_n CONHR$ wherein n is O or 1 and R is hydrogen or alkyl, are described in the Journal of Medicinal Chemistry, 1982, 25, 1300-1307.

We have now found that certain phenol derivatives which are based on the hexoestrol nucleus but which bear an amidic or other function separated from the nucleus by an extended alkylene chain possess potent antioestrogenic activity.

According to the invention there is provided a phenol derivative of the formula:

NU—A—X—$R^1$ where NU is a bis-phenolic nucleus of the general formula

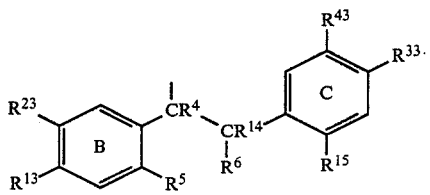

wherein one of $R^{13}$ and $R^{23}$, and one of $R^{33}$ and $R^{43}$, has the formula $R^3O$—, wherein each $R^3$, which may be the same or different, is hydrogen or alkyl, cycloalkyl, alkanoyl, alkoxycarbonyl, carboxyalkanoyl or aroyl each of up to 10 carbon atoms, and wherein the other of $R^{13}$ and $R^{23}$, and the of $R^{33}$ and $R^{43}$, is hydrogen;

wherein $R^4$ and $R^{14}$, which may be the same or different, each is hydrogen or alkyl of up to 5 carbon atoms, or $R^4$ and $R^{14}$ are joined together so that $CR^4$—$CR^{14}$ is an olefinic double bond;

wherein either $R^5$ and $R^{15}$ are both hydrogen and $R^6$ is alkyl of up to 5 carbon atoms;

or $R^5$ and $R^6$ together form a direct link or —$CH_2$—, —$CH(CH_3)$—, —$CH_2CH_2$—, —$(CH_2)_3$—, —CH═CH—, —S—, —O—, —O—$CR_2$—, —O—CO—, —NR—$CH_2$— or —N═CH— wherein R, the two values of which may be the same or different in —$OCR_2$—, is hydrogen or alkyl of up to 3 carbon atoms and $R^{15}$ is hydrogen;

or $R^{15}$ and $R^6$ together form —$CH_2$— and $R^5$ is hydrogen;

and wherein the aromatic rings B and C each may optionally bear one or more halogen or alkyl substituents;

wherein A is straight- or branched-chain alkylene, alkenylene or alkynylene each of from 4 to 12 carbon atoms;

or A has the formula:

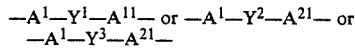

—$A^1$—$Y^1$—$A^{11}$— or —$A^1$—$Y^2$—$A^{21}$— or
—$A^1$—$Y^3$—$A^{21}$— wherein $A^1$ and $A^{11}$ are each alkylene or alkenylene having together a total of 3 to 11 carbon atoms and $Y^1$ is —O—, —S—, —SO—, —$SO_2$— or —CO—;

or $A^1$ is alkylene or alkenylene and $A^{21}$ is a direct link or alkylene, alkenylene or cycloalkylene, such that $A^1$ and $A^{21}$ together have a total of 2 to 10 carbon atoms, and $Y^2$ is —NRCO—, —CONR—, —COO— or —OCO—, wherein R has the meaning stated above, or $Y^3$ is phenylene or naphthylene which may optionally bear one or more halogen or alkyl substituents, or A has the formula:

—$A^1$—$Y^1$—$A^{21}$—$Y^3$—$A^{31}$— or
—$A^1$—$Y^3$—$A^{21}$—$Y^1$—$A^{11}$— wherein $A^1$ and $A^{11}$ are each alkylene or alkenylene, and $A^{21}$ and $A^{31}$ are each a direct link or alkylene or alkenylene, such that $A^1$, $A^{21}$ and $A^{31}$ together, or $A^1$, $A^{21}$ and $A^{11}$ together, have a total of 1 to 9 carbon atoms, and $Y^1$ and $Y^3$ have the meanings stated above;

wherein $R^1$ is hydrogen, or alkyl, alkenyl, cycloalkyl, halogenoalkyl, aryl or arylalkyl each of up to 10 carbon atoms, or $R^1$ is joined to $R^2$ as defined below;

and wherein X is —$CONR^2$—, —$CSNR^2$—, —$NR^1$-$_2CO$—, —$NR^{12}CS$—, —$NR^{12}CONR^2$—,

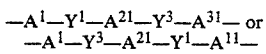

—$SO_2NR^2$— or —CO—, or, when $R^1$ is not hydrogen, is —$NR^{12}COO$—, —S—, —SO— or —$SO_2$—, wherein $R^2$ is hydrogen or alkyl of up to 6 carbon atoms, or $R^1$ and $R^2$ together form alkylene such that, with the adjacent nitrogen atom, they form a heterocyclic ring of 5 to 7 ring atoms, one of which may be a second heterocyclic atom selected from oxygen, sulphur and nitrogen; wherein $R^{12}$ is hydrogen or alkyl of up to 6 carbon atoms;

and wherein $R^{22}$ is hydrogen, cyano or nitro;

or a salt thereof when appropriate.

It will be observed that except when $R^4$ and $R^{14}$ are joined together so that $CR^4$-$CR^{14}$ is an olefinic double bond, the phenol derivative of the invention possesses at least two asymmetric carbon atoms, namely those which bear the substituents $R^4$ and $R^{14}$, and it can therefore exist in racemic and optically-active forms. It is to be understood that this invention encompasses any racemic form of the phenol derivative, and any optically active form thereof, which possesses antioestrogenic activity, it being a matter of common general knowledge how a racemic compound may be separated into its optically-active forms, and how the antioestrogenic properties of any such form may be determined.

A suitable value for the one or more halogen or alkyl substituent in ring B or C, or in the phenylene or naphthalene group —$Y^3$—, is, for example, fluoro, chloro, bromo, iodo, methyl or ethyl.

Preferably $R^{23}$ and $R^{43}$ are hydrogen and $R^{13}$ and $R^{33}$ have the formula $R^3O$—.

A suitable value for $R^3$ when it is cycloalkyl, alkanoyl, alkoxycarbonyl, carboxyalkanoyl or aroyl is, for example, cyclopentyl, formyl, acetyl, propionyl, butyryl, pivaloyl, decanoyl, isopropoxycarbonyl, succinyl, glutaryl or benzoyl. $R^3$ is preferably hydrogen or alkanoyl or alkoxycarbonyl each of up to 5 carbon atoms, especially hydrogen.

A suitable value for R, $R^3$, $R^4$ or $R^{14}$ when it is alkyl is, for example, methyl or ethyl. R and $R^4$ are preferably hydrogen and $R^{14}$ is preferably hydrogen or methyl, or R is hydrogen and $R^4$ and $R^{14}$ are joined together.

A suitable value for $R^6$ when it is alkyl is, for example, methyl, ethyl or n-propyl.

One preferred value for the group —A— is a straight-chain alkylene group of the formula

wherein n is an integer of from 4 to 12, especially from 5 to 11.

A second preferred value for the group A is a group of the formula

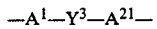

wherein $A^1$ is straight-chain alkylene or alkenylene each of 2 to 9 carbon atoms, especially alkylene of 3 to 6 carbon atoms, —Y— is phenylene (ortho, meta- or, especially, para-) and $A^{21}$ is a direct link, methylene, ethylene, trimethylene or vinylene, especially ethylene.

A suitable value for $R^1$ when it is alkyl, alkenyl or cycloalkyl is, for example, methyl, ethyl, n-propyl, isopropyl, n-butyl, isobutyl, t-butyl, n-pentyl, isopentyl, t-pentyl, 2,2-dimethylpropyl, 1-methylbutyl, 2-methylbutyl, n-hexyl, 1,1-dimethylbutyl, 1,3-dimethylbutyl, n-heptyl, n-decyl, allyl, cyclopentyl or cyclohexyl.

A suitable value for $R^1$ when it is aryl or aralkyl is, for example, phenyl, o-ethylphenyl, p-chlorophenyl, m-chlorophenyl, p-cyanophenyl, p-hydroxyphenyl, p-methoxyphenyl, benzyl, α-methylbenzyl, p-chlorobenzyl, p-methylbenzyl, 3,4-dichlorobenzyl, p-cyanobenzyl, p-methylthiobenzyl, p-trifluoromethylbenzyl, phenethyl, p-fluorophenethyl or p-chlorophenethyl.

A suitable value for $R^1$ when it is halogenoalkyl is, for example, 2-chloro-2,2-difluoroethyl, 2,2,2-trifluoroethyl, 1H,1H-heptafluorobutyl, 4,4,5,5,5-pentafluoropentyl or 1H,1H,2H,2H,3H,3H-heptafluorohexyl.

A suitable value for the heterocyclic ring —$NR^1R^2$ is, for example, pyrrolidino, piperidino, 4-methylpiperidino, 3-methylpiperidino, morpholino or 4-methylpiperazino.

A suitable value for $R^2$ or $R^{12}$ when it is alkyl is, for example, methyl, ethyl or n-butyl.

One appropriate salt is an acid-addition salt of a phenol derivative which possesses a basic function, for example a compound wherein $R^5$ and $R^6$ together form —NR—$CH_2$— or —N=CH—. A suitable acid-addition salt is, for example, a hydrochloride, hydrobromide, acetate, citrate, oxalate or tartrate.

Another appropriate salt is a base-addition salt of a phenol derivative which possesses a carboxy function, for example a compound wherein $R^3$ is carboxyalkanoyl. A suitable base-addition salt is, for example, a sodium, potassium, ammonium or cyclohexylamine salt.

A preferred phenol derivative of the invention has the formula stated above wherein both $R^3$ substituents and $R^{15}$ are all hydrogen, wherein either $R^4$ is hydrogen and $R^{14}$ is hydrogen, methyl or ethyl, or $R^4$ and $R^{14}$ are joined together, wherein either $R^5$ is hydrogen and $R^6$ is methyl, ethyl or n-propyl, or $R^5$ and $R^6$ together form —$CH_2$—, —$CH_2CH_2$—, —$CH(CH_3)$—, —CH=CH— or —S—, wherein —A— is —$(CH_2)_n$—, wherein n is an integer from 4 to 12, especially from 5 to 11, or —A— is

wherein p is an integer from 2 to 9, especially from 3 to 6, q is 0 to 3, especially 2, and the —$(CH_2)_q$—group is in the meta- or, especially, the para-position; wherein $R^1$ is alkyl or fluoroalkyl each of 4 to 10 carbon atoms, especially of 4 to 7 carbon atoms, or phenyl or chlorophenyl, or alkyl of 1 to 3 carbon atoms which bears a phenyl, tolyl, halogenophenyl or trifluoromethylphenyl substituent, or is linked to $R^2$ as stated below;

wherein X is —$CONR^2$—, —S—, —SO— or —$SO_2$—, wherein $R^2$ is hydrogen or alkyl of up to 3 carbon atoms or together with $R^1$ forms alkylene of 5 or 6 carbon atoms;

and wherein ring C may optionally bear one or two methyl substituents.

A particularly preferred phenol derivative of the invention has the formula stated above wherein the number of carbon atoms in the two groups A and $R^1$ adds up to between 11 and 21, especially 14 to 16 if neither $R^1$ nor A contains a phenyl or phenylene group, 17 to 19 if there is either a phenylene group in —A— or a phenyl group in $R^1$, and 19 to 21 if there are both a phenylene group in —A— and a phenyl group in $R^1$.

An especially preferred phenol derivative of the invention has the formula stated above wherein:

NU is 6-hydroxy-2-p-hydroxyphenylnaphth-1-yl and A is —$(CH_2)_{10}$—, —$(CH_2)_{11}$— or —$(CH_2)_5$—(1,4-phenylene)—$(CH_2)_2$—;

or NU is 1,2,3,4-tetrahydro-6-hydroxy-2-p-hydroxyphenylnaphthyl-1-yl (either 1RS, 2RS or 1RS, 2SR isomer), or 1,2,3,4-tetrahydro-6-hydroxy-2-p-hydroxyphenyl-2-methylnaphth-1-yl (either 1RS, 2RS or 1RS, 2SR isomer), and A is —$(CH_2)_{10}$—, —$(CH_2)_{11}$— or —$(CH_2)_4$—(1,4-phenylene)—$(CH_2)_2$—;

or NU is (1RS, 2RS)-5-hydroxy-2-p-hydroxyphenylindan-1-yl or (1RS, 2RS)-5-hydroxy-2-p-hydroxyphenyl-2-methylindan-1-yl and A is —$(CH_2)_{10}$—, —$(CH_2)_{11}$— or, —$(CH_2)_4$—(1,4-phenylene)—$(CH_2)_2$—;

and wherein X is —$CONR^1R^2$ wherein $R^2$ is hydrogen or methyl and $R^1$ is n-butyl, 1H, 1H-heptafluorobutyl, n-pentyl or n-hexyl, or X is —$SR^1$, $SOR^1$ or —$SO_2R^1$ wherein $R^1$ is n-pentyl, n-hexyl, 4,4,5,5,5-pentafluoropentyl or 1H,1H,2H,2H,3H,3H-heptafluorohexyl.

Specific phenol derivatives of the invention are hereinafter described in the Examples. Of these, particularly preferred compounds are:

N-n-butyl-, N-n-butyl-N-methyl-, N-n-pentyl-, N-(1H,1H-heptafluorobutyl)- and N-(1H,1H-heptafluorobutyl)-N-methyl-3-p-[5-(6-hydroxy-2-p-hydroxyphenylnaphth-1-yl)pentyl]-phenylpropionamide;

(1RS, 2RS)-1-{4-[p-(2-n-hexylthioethyl)phenyl]butyl}-2-p-hydroxyphenyl-1,2,3,4-tetrahydronaphth-6-ol and the corresponding 4,4,5,5,5-pentafluoropentylthio derivative, and the corresponding hexylsulphinyl, hexylsulphonyl and pentafluorohexylthio derivatives;

2-p-hydroxyphenyl-1-{5-[p-(3-n-hexylthioethyl)-phenyl]pentyl} naphth-6-ol and the corresponding hexylsulphinyl derivative;

N-methyl-N-(1H,1H-heptafluorobutyl)-p-{4-[(1RS,2RS)-6-hydroxy-2-p-hydroxyphenyl-2-methyl-1,2,3,4-tetrahydronaphth-1-yl]butyl}phenylpropionamide;

(1RS,2RS)-1-{4-[p-(2-n-hexylthioethyl)phenyl]butyl}-2-p-hydroxyphenyl-2-methyl-1,2,3,4-tetrahydronaphth-6-ol and the corresponding 4,4,5,5,5-pentafluorohexylthio derivative, and the correponding hexylsulphonyl and pentafluoropentylsulphinyl derivative, and the corresponding (1RS, 2SR) isomers of both the hexylthio and hexylsulphinyl derivatives; and (8RS, 9SR)-8,9-di-p-hydroxyphenyl-N-n-octyl-dodecanamide.

A preferred process for the manufacture of a phenol derivative of the invention wherein X has the formula $-CONR^2-$, $-CSNR^2-$ or $-SO_2NR^2-$ comprises the reaction of a compound of the formula $NU^1-A-Z^1$, wherein A has the meaning stated above, wherein $NU^1$ has the same meaning as stated above for NU except that the hydroxy groups are protected and wherein $Z^1$ is an activated group derived from a carboxylic, thiocarboxylic or sulphonic acid, with an amine of the formula $HNR^1R^2$, wherein $R^1$ and $R^2$ have the meanings stated above, whereafter the protecting groups in $NU^1$ are removed by conventional means. A suitable activated group $Z^1$ is, for example, a mixed anhydride, for example an anhydride formed by reaction of the acid with a chloroformate such as isobutyl chloroformate.

A suitable protecting group in $NU^1$ is, for example, an alkyl or aralkyl ether, for example the methyl or benzyl ether, or a tetrahydropyranyl ether, of both of the hydroxy functions. The methyl ether is preferred, and the methyl group is preferably removed with boron tribromide.

A preferred process for the manufacture of a phenol derivative of the invention wherein X has the formula $-CO-$ comprises the reaction of an acid of the formula $NU^1-A-COOH$, wherein $NU^1$ and A have the meanings stated above, with an organometallic compound of the formula $R^1-M$, wherein $R^1$ has the meaning stated above and M is a metal group, for example the lithium group, whereafter the protecting groups in $NU^1$ are removed by conventional means.

A preferred process for the manufacture of a phenol derivative of the invention wherein X has the formula $-S-$ comprises the reaction of a compound of the formula $NU^1-A-Z^2$, wherein $NU^1$ and A have the meanings stated above and wherein $Z^2$ is a displaceable group, with a compound of the formula $R^1SH$, wherein $R^1$ has the meaning stated above, whereafter the protecting groups in $NU^1$ are removed by conventional means.

A suitable value for $Z^2$ is, for example, a halogen atom or a sulphonyloxy group, for example the methanesulphonyloxy or toluene-p-sulphonyloxy group.

A preferred process for the manufacture of a phenol derivative of the invention wherein X has the formula $-NR^{12}CO-$, $-NR^{12}CS-$, $-NR^{12}CONR^2-$, $$-NR^{12}-\overset{\overset{NR^{22}}{\|}}{C}-NR^2-$$

or $-NR^{12}COO-$ comprises the reaction of a compound of the formula $NU^1-A-NHR^{12}$, wherein $NU^1$, A and $R^{12}$ have the meanings stated above, with an acylating agent derived from an acid of the formula $R^1COOH$, $R^1CSOH$ or $R^1OCOOH$, or, for the manufacture of a urea, with an isocyanate of the formula $R^1NCO$; or, for the manufacture of a guanidine, with a cyanamide of the formula $R^1NR^2-CN$, whereafter the protecting groups in $NU^1$ are removed by conventional means.

A suitable acylating agent is, for example, an acyl chloride or acyl anhydride.

The starting materials for use in all the abovementioned processes may be obtained by elaborating the side-chain $-A-COOH$ or $-A^2-CH_2OH$ onto the nucleus $NU^1$ by conventional means. Detailed methods for carrying out such an elaboration are hereinafter provided in the Examples, but in general terms a compound of the formula:

$$Z^2-A-COOR^7 \text{ or}$$
$$Z^2-A^2-CH_2OSi(CH_3)_2C(CH_3)_3 \text{ or}$$
$$HC\equiv C-A^{22}-CH_2OSi(CH_3)_2C(CH_3)_3$$

wherein A and $Z^2$ have the meanings stated above, wherein $A^2$ is such that $-A^2CH_2-$ has the same meaning as A, wherein $A^{22}$ is such that $-CH_2CH_2A^{22}CH_2-$ has the same meaning as A, and wherein $R^7$ is hydrogen or alkyl of up to 6 carbon atoms, may be reacted with a suitable compound which is, or which may be converted into, $NU^1H$, or a compound of the formula:

$$NU^1-A^3-CHO$$

wherein $NU^1$ has the meaning stated above and wherein $A^3$ is a direct link or alkylene, may be reacted with a diethylphosphonate of the formula:

$$(C_2H_5O)_2\overset{\overset{O}{\|}}{P}CH_2-A^4-COOR^7$$

or a triphenylphosphonium bromide of the formula:

$$(C_6H_5)_3P^+CH_2-A^4-COOR^7 \; Br^-$$

wherein $R^7$ has the meaning stated above and $A^4$ is alkylene or modified alkylene, to provide a compound of the formula;

$$NU^1-A^3-CH=CH-A^4-COOR^7$$

wherein $NU^1$, $A^3$, $A^4$ and $R^7$ have the meanings stated above. This can be used directly to provide a phenol derivative of the invention wherein A contains an olefinic double bond, or it may be reduced to provide a starting material for the preparation of a phenol derivative of the invention wherein $-A^3-(CH_2)_2-A^4-$ has the same meaning as A defined above.

The intermediate of the formula $$NU^1-A^2-CH_2OH$$

wherein $NU^1$ and $A^2$ have the meanings stated above, may be oxidised to the corresponding carboxylic acid of the formula NU¹—A²—COOH which provides the starting material for the first or second process of the invention described above;

or it may be converted into a compound of the formula NU¹—A²—CH₂Z² by reaction with a halogenating agent or a sulphonylating agent to provide the starting material for the third process of the invention described above.

The starting material for the fourth process of the invention described above may be obtained by using the third process of the invention described above except that an amine of the formula R¹²NH₂ is used in place of a thiol of the formula R¹SH.

An alternative process for the manufacture of a phenol derivative of the invention wherein —A— is alkenylene of the formula —A³—CH=CH—A⁴— comprises the reaction of a compound of the formula:

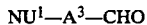

wherein NU¹ and A³ have the meanings stated above, with a triphenylphosphonium salt of the formula:

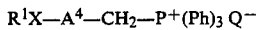

wherein R¹, X and A⁴ have the meanings stated above and wherein Q⁻ is an anion, for example the bromide ion, whereafter the protecting groups in NU¹ are removed by conventional means.

The reaction may be carried out in solution in dimethyl sulphoxide in the presence of dimsyl sodium.

The phosphonium starting material may be obtained by reaction of triphenylphosphine with a bromide of the formula

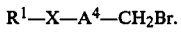

A phenol derivative of the invention wherein either substituent R³ is other than hydrogen may be obtained from the corresponding compound wherein either substituent R³ is hydrogen by conventional etherification or esterification processes, and these may also be used in reverse to prepare the corresponding hydroxy compounds.

A phenol derivative of the invention wherein A is alkenylene may be hydrogenated to provide the corresponding compound wherein A is alkylene.

A phenol derivative of the invention wherein —X— is —CSNH— or —NHCS— may be obtained by the reaction of the corresponding compound wherein X is —CONH— or —NHCO— with 2,4-bis-(4-methoxyphenyl)-1,3-dithia-2,4-diphosphetane-2,4-disulphide.

A phenol derivative of the invention wherein X is —SO— or —SO₂— may be obtained by the oxidation of the corresponding compound wherein X is —S—. The conditions for the oxidation will be chosen to provide the desired product; for example aqueous sodium metaperiodate will oxidise the sulphur group to sulphinyl, and m-chloroperbenzoic acid in chloroform solution will oxidise the sulphur group to sulphonyl.

A phenol derivative of the invention wherein R⁵ and R⁶ form —CH₂CH₂— and either R⁴ and R¹⁴ are both hydrogen, or R⁴ and R¹⁴ are joined together so that CR⁴—CR¹⁴ is an olefinic double bond, may be converted into a phenol derivative of the invention wherein both —CR⁴—CR¹⁴— and —R⁵—R⁶— are —CH=CH— (that is, a naphthalene derivative) by aromatisation by conventional means, for example with 2,3-dichloro-5,6-dicyano-1,4-benzoquinone.

As stated above, a phenol derivative of the invention possesses antioestrogenic activity. This may be demonstrated by its effect in antagonising the increase in weight of the uterus of an immature female rat produced by administering oestradiol benzoate to said rat. Thus, when a phenol derivative of the invention and oestradiol benzoate are co-administered for 3 days to such a rat, a smaller increase in uterine weight is produced than the substantial increase which would be produced by the administration of oestradiol benzoate without the phenol derivative of the invention.

In particular, a preferred phenol derivative of the invention produces an antioestrogenic effect at a dose which produces no partial agonist effect, unlike the known antioestrogens tamoxifen and clomiphene. When a preferred phenol is coadministered with oestradiol benzoate to a rat as described above, no increase in uterine weight whatsoever is observed at a suitable dose.

A compound with the above pharmacological properties is of value in the treatment of the same conditions in which tamoxifen is beneficial, in particular, in the treatment of anovulatory infertility and in the treatment of breast tumours. It is also of value in the treatment of menstrual disorders.

When used to produce an anti-oestrogenic effect in warm-blooded animals, a typical daily dose is from 0.1 to 25 mg/kg. administered orally or by injection. In man this is equivalent to an oral dose of from 5 to 1250 mg./day. A phenol derivative of the invention is most conveniently administered to man in the form of a pharmaceutical composition.

According to a further feature of the invention, there is provided a pharmaceutical composition comprising a phenol derivative of the invention together with a pharmaceutically acceptable diluent or carrier.

The composition may be in a form suitable for oral or parenteral administration. A tablet or capsule is a particularly convenient form for oral administration and such a composition may be made by conventional methods and contain conventional excipients. Thus a tablet could contain diluents, for example mannitol or maize starch, disintegrating agents, for example alginic acid, binding agents, for example methyl-cellulose, and lubricating agents, for example magnesium stearate.

The composition may contain, in addition to the phenol derivative of the invention, one or more antiandrogenic agents or antiprogestational agents.

A composition for oral administration may conveniently contain from 5 to 500 mg. of a phenol derivative of the invention.

The invention is illustrated but not limited by the following Examples:

EXAMPLE 1

A solution of isobutyl chloroformate (0.09 g.) in methylene chloride (5 ml.) was added to a stirred solution of 11-(6-methoxy-2-p-methoxyphenylnaphth-1-yl)undecanoic acid (0.25 g.) and N-methylmorpholine (0.17 g.) in methylene chloride (10 ml.) which was cooled to −30° C., and the mixture was allowed to warm up to laboratory temperature. A solution of N-methylbutylamine (0.073 g.) in methylene chloride (5 ml.) was added and the mixture was stirred for 2 hours, neutralised with aqueous 2N-hydrochloric acid (15 ml.) and extracted three times with diethyl ether (30 ml.

each time). The combined extracts were washed with water, dried and evaporated to dryness and the residue was purified by chromatography on a silica gel column using a 100:1 v/v mixture of methylene chloride and methanol as eluant. A solution of boron tribromide (0.48 g.) in methylene chloride (3 ml.) was added to a stirred solution of the N-butyl-11-(6-methoxy-2-p-methoxyphenylnaphth-1-yl)-N-methylundecanamide thus obtained (0.2 g.) in methylene chloride (10 ml.) which was cooled to −30° C. under an atmosphere of argon, and the mixture was allowed to warm up to 0° C. and was stirred at that temperature for 2 hours. Water (10 ml.) was added, the mixture was extracted three times with diethyl ether (20 ml. each time) and the combined extracts were washed with water, dried and evaporated to dryness. The residue was purified by chromatography on a silica gel column using a 100:3 v/v mixture of methylene chloride and methanol as eluant. There was thus obtained as an oil N-butyl-11-(6-hydroxy-2-p-hydroxyphenylnaphth-1-yl)-N-methylundecanamide, the structure of which was confirmed by proton magnetic resonance and mass spectroscopy as follows:

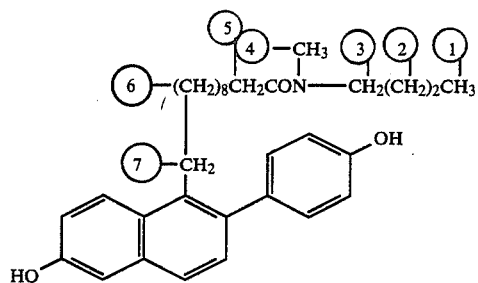

Proton Magnetic Resonance Spectrum (90 megahertz in deuterochloroform)

| Shift (delta) | Type of Peak | No of H.Atoms | Specific H Atoms |
|---|---|---|---|
| 0.92 | t | 3 | 1 |
| 0.94 | t | | |
| 1.05–1.80 | broad m | 20 | 2, 6 |
| 2.37 | t | 2 | 5 |
| 2.80–3.05 | m, 2s | 5 | 4, 7 |
| 3.30 | m | 2 | 3 |
| 6.18 | broad s | 1 | (OH) |
| 6.85–7.31 | m | 7 | |
| 7.50 | d | 1 | (aromatic H) |
| 7.96 | d | 1 | |
| 8.42 | broad s | 1 | (OH) |

Mass Spectrum: Parent ion m/e 489, Exact Mass 489.3264 $C_{32}H_{43}NO_3$ requires 489.3242.

Other ions at Mass No. 402,249.

Infra-red Spectrum: Peaks at 3500–3200 cm$^{-1}$(OH); 1620 cm$^{-1}$ (amide).

All other final compounds falling within the scope of the invention and hereinafter described in the following examples were similarly examined by proton magnetic resonance and mass spectroscopy and their structures were confirmed by these techniques.

The 11-(6-methoxy-2-p-methoxyphenylnaphth-1-yl)undecanoic acid used as starting material was obtained as follows:

A mixture of 3,4-dihydro-6-methoxynaphthalen-2(1H)-one (10 g.), pyrrolidine (8.1 g.) and toluene (150 ml.) was stirred and heated under reflux for 3 hours in a Dean and Stark water-separating apparatus, and the toluene was then removed by evaporation. A mixture of the residue (13 g.), t-butyl 11-iodoundecanoate (31.5 g.) and dioxan (150 ml.) was stirred and heated under reflux for 96 hours, water (50 ml.) and acetic acid (2 ml.) were added and the mixture was heated at 100° C. for 1 hour and then concentrated by evaporation. The residue was extracted three times with diethyl ether (150 ml. each time) and the combined extracts were washed with water, dried and evaporated to dryness. The residue was purified by chromatography on a silica gel column using a 2:1 v/v mixture of petroleum ether (b.p. 40°–60° C.) and diethyl ether as eluant. There was thus obtained as an oil t-butyl 11-(3,4-dihydro-6-methoxy-2-oxonaphth-1-yl)undecanoate.

A Grignard reagent was prepared from 4-bromoanisole (13.5 g.) and magnesium turnings (1.75 g.) in diethyl ether (105 ml.) and was heated under reflux for 30 minutes and then diluted with tetrahydrofuran (50 ml.). A solution of the above 5-butyl undecanoate (7.5 g.) in tetrahydrofuran (80 ml.) was added to half of the Grignard reagent, the rest of the Grignard reagent was then added and the mixture was stirred at laboratory temperature for 90 minutes. Saturated aqueous ammonium chloride solution (50 ml.) was added and the mixture was extracted three times with diethyl ether (150 ml. each time). The combined extracts were washed with water, dried and evaporated to dryness and the residue was purified by chromatography on a silica gel column using a 20:1 v/v mixture of toluene and ethyl acetate as eluant. There was thus obtained as an oil t-butyl 11-(3,4-dihydro-2-hydroxy-6-methoxy-2-p-methoxyphenyl-naphth-1-yl)undecanoate.

A mixture of the above ester (3.3 g.), 2,3-dichloro-5,6-dicyano-1,4-benzoquinone (1.7 g.) and toluene (150 ml.) was heated under reflux for 1 hour in a Dean and Stark water-separating apparatus, and then cooled and filtered through a filter-aid. The filtrate was evaporated to dryness and the residue was purified by chromatography on a silica gel column using a 25:1 v/v mixture of methylene chloride and methanol as eluant. There was thus obtained 11-(6-methoxy-2-p-methoxyphenyl-naphth-1-yl)undecanoic acid.

EXAMPLE 2

The process described in Example 1 was repeated using the appropriate amine and the appropriate omega-naphthylalkanoic acid derivative as starting materials. There were thus obtained as oils the compounds described in the following tables, the structures of which were confirmed by proton magnetic resonance and mass spectroscopy:

TABLE I

| n | $R^1$ | $R^2$ |
|---|---|---|
| 11 | n-butyl | H |
| 11 | n-butyl | methyl |
| 11 | 1H,1H—heptafluorobutyl | H |
| 10 | n-butyl | H |
| 10 | n-pentyl | H |
| 10 | 1H,1H—heptafluorobutyl | H |
| 10 | 1H,1H—heptafluorobutyl | methyl |

TABLE I-continued

[Structure: naphthalene with CONR¹R² on (CH₂)n substituent, HO group, and phenyl-OH group]

| n | R¹ | R² |
|---|------|---|
| 7 | n-octyl | H |

TABLE 2

[Structure: tetrahydronaphthalene with CONR¹R² on (CH₂)n substituent, HO group, and phenyl-OH group]

| n | R¹ | R² |
|---|------|---|
| 11 | n-butyl | H |
| 11 | n-butyl | methyl |
| 11 | 1H,1H—heptafluorobutyl | H |
| 10 | 1H,1H—heptafluorobutyl | H |
| 10 | n-pentyl | H |
| 8 | n-heptyl | H |
| 7 | n-heptyl | H |
| 7 | n-octyl | H |

The alkanoic acid used as starting material was obtained either as described in Example 1, or by a procedure exemplified by the following preparation of a dodecanoic acid:

A solution of phosphorus oxychloride (0.2 ml.) in methylene chloride (15 ml.) was added slowly to a stirred solution of propargyl alcohol (42 g.) and dihydropyran (64 g.) in methylene chloride (120 ml.) which was cooled to 0° C., and the mixture was stirred at that temperature for 30 minutes. Diethyl ether (120 ml.) was added and the mixture was washed twice with saturated aqueous sodium bicarbonate solution (50 ml. each time) and once with saturated aqueous sodium chloride solution (50 ml.), dried and evaporated to dryness. The residue was distilled at 80°-86° C./10 mm.Hg. and further purified by chromatography through an alumina column.

A solution of methyl magnesium iodide (22.3 ml. of a 2.86 molar solution in tetrahydrofuran) was added dropwise to a stirred solution of the propargyl tetrahydropyranyl ether thus obtained (10.0 g.) in tetrahydrofuran (200 ml.) which was maintained under an atmosphere of argon, and the mixture was heated under reflux for 30 minutes. A solution of 3,4-dihydro-6-methoxy-2-p-methoxyphenylnaphthalen-1(2H)-one (7.2 g.; prepared by the method described in the Journal of Medicinal Chemistry, 1966, 9, 172) in tetrahydrofuran (100 ml.) was added to the boiling solution and the mixture was heated under reflux for 30 minutes, cooled and poured into ice-cold saturated aqueous ammonium chloride solution (300 ml.). The mixture was extracted three times with diethyl ether (150 ml. each time) and the combined extracts were washed with water, dried and evaporated to dryness. The residue was purified by chromatography on a silica gel column using a 5:1 v/v mixture of toluene and ethyl acetate as eluant. There was thus obtained as an oil 6-methoxy-2-p-methoxyphenyl-1,2,3,4-tetrahydro-1-(3-tetrahydropyranyloxypropynyl)naphth-1-ol.

A solution of the above naphthol (10 g.) in ethyl acetate (250 ml.) was stirred in an atmosphere of hydrogen for 90 minutes in the presence of a 10% palladium-on-charcoal catalyst (3 g.). The mixture was filtered, fresh catalyst (3 g.) was added to the filtrate and the mixture was stirred in an atmosphere of hydrogen for a further 90 minutes and then filtered. The filtrate was evaporated to dryness and the residue was purified by chromatography on silica gel column using a 10:1 v/v mixture of toluene and ethyl acetate as eluant. There was thus obtained an an oil (1RS, 2RS)-6-methoxy-2-p-methoxyphenyl-1,2,3,4-tetrahydro-1-(3-tetrahydropyranyloxypropyl)naphthalene.

Aqueous 2N-hydrochloric acid (50 ml.) was added to a stirred solution of the above compound (6.8 g.) in ethanol (200 ml.), and the mixture was stirred and heated under reflux for 2 hours, cooled and evaporated to dryness. Saturated aqueous sodium bicarbonate solution (100 ml.) was added to the residue, and the mixture was extracted three times with ethyl acetate (100 ml. each time). The combined extracts were washed with water, dried and evaporated to dryness and the residue was purified by chromatography on a silica gel column using a 5:1 v/v mixture of toluene and ethyl acetate as eluant. There was thus obtained as an oil 3-[(1RS, 2RS)-6-methoxy-2-p-methoxyphenyl-1,2,3,4-tetrahydronaphth-1-yl]propanol.

Pyridinium chlorochromate (4.86 g.) was added portionwise during 20 minutes to a stirred solution of the above propanol (4.9 g.) in methylene chloride (400 ml.) and the mixture was stirred for 1 hour. Further pyridinium chlorochromate (1.6 g.) was added and the mixture was stirred for 30 minutes and then poured onto a column of silica gel. The column was eluted with 5:1 v/v mixture of toluene and ethyl acetate and the eluate was evaporated to dryness. There was thus obtained as an oil 3-[(1RS, 2RS)-6-methoxy-2-p-methoxyphenyl-1,2,3,4-tetrahydronaphth-1-yl]propionaldehyde.

Methanesulphinyl sodium (10.5 ml. of a 1.4 molar solution in dimethyl sulphoxide) was added dropwise to a stirred solution of (8-carboxyoctyl)triphenylphosphonium bromide (4.6 g., finely powdered and freshly dried by evaporation from it of 100 ml. of toluene) in dimethyl sulphoxide (20 ml.) which was maintained under an atmosphere of nitrogen, and a solution of the above aldehyde (1.0 g.) in tetrahydrofuran (20 ml.) was added. The mixture was stirred for 2 hours and then poured into ice-cold saturated aqueous ammonium chloride solution (50 ml.), and the mixture was extracted three times with ethyl acetate (50 ml. each time). The combined extracts were washed with water, dried and evaporated to dryness and the residue was purified by chromatography on a silica gel column using a 2:1 v/v mixture of toluene and ethyl acetate as eluant. There was thus obtained as an oil 12-[(1RS, 2RS)-6-methoxy-2- p-methoxyphenyl-1,2,3,4-tetrahydronaphth-1-yl]dodec-9- enoic acid.

A solution of the above acid (0.72 g.) in ethyl acetate (50 ml.) was stirred for 30 minutes under an atmosphere of hydrogen in the presence of a 10% palladium-on-charcoal catalyst (0.3 g.). The mixture was filtered and the filtrate was evaporated to dryness. There was thus obtained as residue 12-[(1RS, 2RS)-6-methoxy-2-p-methoxyphenyl-1,2,3,4-tetrahydronaphth-1yl]-dodecanoic acid, which was a starting material for compounds described in Table 2. All compounds described in Table 2 have the (1RS, 2RS) relative configuration.

The starting materials for the compounds described in Table 2 wherein n is 7 or 8 were obtained by a similar sequence of processes to those described above, except that (4-carboxybutyl)- or (5carboxypentyl)triphenylphosphonium bromide respectively was used in the penultimate step in place of the (8-carboxyoctyl)-compound.

2,3-Dichloro-5,6-dicyano-1,4-benzoquinone (0.31 g.) and p-toluenesulphonic acid (0.005 g.) were successively added to a stirred solution of 12-[(1RS, 2RS)-6-methoxy-2-p-methoxyphenyl-1,2,3,4-tetrahydronaphth-1-yl]dodecanoic acid (0.29 g.) in benzene (30 ml.), and the mixture was stirred and heated under reflux for 2 hours whilst a stream of argon was bubbled through it. The mixture was cooled and filtered, the filtrate was evaporated to dryness and the residue was purified by chromatography on a silica gel column using a 2:1 v/v mixture of toluene and ethyl acetate as eluant. There was thus obtained as an oil 12-(6-methoxy-2-p-methoxyphenylnaphth-1-yl)dodecanoic acid, which was a starting material for compounds described in Table 1.

The starting material for the compound described in Table 1 wherein n is 7 was similarly obtained from the corresponding tetrahydro compound prepared using (4-carboxybutyl)triphenylphosphonium bromide.

EXAMPLE 3

The process described in Example 1 was repeated using the appropriate amine and the appropriate naphthyl-alkyl-phenylene-alkanoic acid as starting materials. There were thus obtained the compounds described in the following tables:

TABLE I

| p | q | $R^1$ | $R^2$ |
|---|---|---|---|
| 4 | 2 | n-butyl | H |
| 4 | 2 | n-pentyl | H |
| 4 | 2 | n-hexyl | H |
| 4 | 2 | 1H,1H—heptafluorobutyl | H |
| 4 | 2 | 1H,1H,heptafluorobutyl | methyl |
| 5 | 2 | n-butyl | H |
| 5 | 2 | n-butyl | methyl |
| 5 | 2 | n-pentyl | H |
| 5 | 2 | 1H,1H—heptafluorobutyl | H |
| 6 | 1 | 1H,1H—heptafluorobutyl | methyl |
| 5 | 2 | 3-methylpentamethylene | |

TABLE 2

| p | q | Position in Phenyl ring | $R^8$ | $R^1$ | $R^2$ |
|---|---|---|---|---|---|
| 4 | 2 | 4- | H | n-hexyl | H |
| 4 | 2 | 4- | H | 1H,1H—heptafluorobutyl | H |
| 5 | 2 | 4- | H | n-butyl | H |
| 5 | 2 | 4- | H | n-butyl | methyl |
| 5 | 2 | 4- | H | n-pentyl | H |
| 5 | 2 | 4- | H | 1H,1H—heptafluorobutyl | H |
| 5 | 2 | 4- | H | 1H,1H—heptafluorobutyl | methyl |
| 5 | 2 | 4- | H | p-chlorobenzyl | H |
| 5 | 2 | 4- | H | p-chlorobenzyl | methyl |
| 5 | 2 | 3- | H | n-hexyl | H |
| 5 | 2 | 3- | H | 1H,1H—heptafluorobutyl | H |
| 5 | 2 | 3- | H | 1H,1H—heptafluorobutyl | methyl |
| 5 | 2 | 4- | chloro | n-butyl | methyl |
| 5 | 2 | 4- | chloro | 1H,1H—heptafluorobutyl | H |
| 5 | 2 | 4- | chloro | 1H,1H,heptafluorobutyl | methyl |
| 5 | 1 | 4- | H | 1H,1H—heptafluorobutyl | methyl |
| 6 | 1 | 4- | H | 1H,1H—heptafluorobutyl | methyl |
| 5 | 2 | 4- | H | 3-methylpentamethylene | |

The phenylenealkanoic acids used as starting materials were obtained as follows: 3-p-[4-(6-Methoxy-2-p-methoxyphenylnaphth-1-yl)butyl]phenylpropionic acid and its (1RS, 2RS)1,2,3,4-tetrahydro derivative.

n-Butyl-lithium (2.2 ml. of a 1.5 molar solution in hexane) was added dropwise to a stirred solution of diisopropylamine (0.42 g.) in tetrahydrofuran (30 ml.) which was cooled to −70° C. under an atmosphere of argon, the mixture was stirred for 15 minutes and a solution of ethyl p-(diethoxyphosphonylmethyl)cinnamate (1.2 g; b.p. 175° C./15 mm.Hg.; prepared by heating ethyl p-bromomethylcinnamate with triethyl phosphite at 120° C. for 2 hours) in tetrahydrofuran (10 ml.) was added. The mixture was stirred at −70° C. for 10 minutes and a solution of 3-[(1RS, 2RS)-6-methoxy-2-p-methoxyphenyl1,2,3,4-tetrahydronaphth-1-yl]propionaldehyde (0.3 g; Example 2; 5th paragraph in respect of preparation of starting materials) in tetrahydrofuran (5 ml.) was added. The mixture was allowed to warm up to 0° C., stirred at that temperature for 1 hour and then poured into saturated aqueous ammonium chloride solution (30 ml.). The mixture was extracted three times with ethyl acetate (50 ml. each time) and the combined extracts were washed with water, dried and evaporated to dryness. The residue was purified by chromatography on a silica gel column using a 10:1 v/v mixture of toluene and ethyl acetate as eluant. There was thus obtained as an oil ethyl p-{4-[(1RS, 2RS)-6-methoxy-2-p-methoxyphenylethyl-1,2,3,4-tetrahydronaphth-1-yl]but-1-enyl}cinnamate.

A solution of the above compound (0.35 g.) in ethyl acetate (20 ml.) was stirred under an atmosphere of hydrogen for 1 hour in the presence of a 10% palladium-on-charcoal catalyst (0.15 g.). The mixture was filtered, the filtrate was evaporated to dryness and the residue was dissolved in methanol (20 ml.). Aqueous 3N-potassium hydroxide solution (8 ml.) was added, the mixture was stirred at laboratory temperature for 16 hours and the methanol was removed by evaporation. The residue was acidified with aqueous 2N-hydrochloric acid and extracted three times with ethyl acetate (20 ml. each time). The combined extracts were washed with water, dried and evaporated to dryness and the residue was purified by chromatography on a silica gel column using a 2:1 v/v mixture of toluene and ethyl acetate as eluant. There was thus obtained 3-p-[4-([1RS, 2RS]-6-methoxy-2-p-methoxyphenyl-1,2,3,4-tetrahydronaphth-1yl)butyl]phenylpropionic acid, which was used as starting material for the preparation of compounds in Table I wherein p is 4 and q is 2.

The above acid (0.2 g.) was reacted with 2,3-dichloro-5,6-dicyano-1,4-benzoquinone (0.22 g.) by a similar process to that described in the penultimate paragraph of Example 2. There was thus obtained 3-p-[4-(6- methoxy-2-p-methoxyphenylnaphth-1-yl]-phenyl-propionic acid which was used as starting material for the preparation of compounds wherein p is 4 and q is 2.

3-p-[5-(6-Methoxy-2-p-methoxyphenylnaphth-1-yl)pentyl]phenylpropionic acid and its (1RS, 2RS)-1,2,3,4-tetrahydro-derivative.

These were obtained by a similar process to that described above except that 4-[(1RS,2RS)-6-methoxy 2-p- methoxyphenyl-1,2,3,4-tetrahydronaphth-1-yl]butyraldehyde was used as starting material in place of corresponding propionaldehyde. The butyraldehyde was obtained by a similar process to that described in the second part of Example 2 except that but-3-ynyl tetrahydropyranyl ether was used in place of propargyl tetrahydropyranyl ether.

3-m-[5-(6-Methoxy-2-p-methoxyphenylnaphth-1-yl)pentyl]phenylpropionic acid

This was obtained by a similar process to that decribed above except that the butyraldehyde was reacted with ethyl m-(diethoxyphosphonylmethyl)cinnamate.

3{3-Chloro-4-[5-(6-methoxy-2-p-methoxyphenyl-naphth-1-yl)pentyl]phenyl}propionic acid This was obtained by a similar process to that decribed above except that the butyraldehyde was reacted with ethyl 3-chloro-4-(diethoxyphosphonylmethyl)cinnamate. The cinnamate was obtained as follows:

Diisobutylaluminium hydride (11.4 ml. of a 1.8 molar solution in toluene) was added dropwise to a stirred solution of 3-chloro-4-methylbenzonitrile (3.03 g.) in toluene (100 ml.) which was cooled to 0° C. under an atmosphere of argon, and the mixture was stirred at that temperature for 1 hour. Methanol (60 ml.) and aqueous 20% w/v sulphuric acid (60 ml.) were successively added, the mixture was stirred at 0° C. for 30 minutes and the organic layer was separated, washed with water, dried and evaporated to dryness.

Sodium hydride (2.9 g. of a 50% dispersion in mineral oil) was added portionwise to a solution of ethyl diethoxyphosphonylacetate (13.4 g.) in tetrahydrofuran (100 ml.) which was kept under an atmosphere of argon, and the solution thus obtained was added to a solution of the 3-chloro-4-methylbenzaldehyde (3.2 g.) obtained above in tetrahydrofuran (50 ml.). The mixture was stirred at laboratory temperature for 1 hour, aqueous 3N-hydrochloric acid (40 ml.) was added and the mixture was extracted three times with diethyl ether (50 ml. each time). The combined extracts were washed with water, dried and evaporated to dryness and the residue was purified by chromatography on a silica gel column using a 4:3 v/v mixture of petroleum ether (b.p. 40°-60° C.) and methylene chloride as eluant. The solution of the ethyl 3-chloro-4-methylcinnamate thus obtained (2.6 g.) and N-bromosuccinimide (2.3 g.) in carbon tetrachloride (40 ml.) was irradiated with a 100 watt lamp and heated under reflux for 16 hours, cooled and filtered and the filtrate was evaporated to dryness. The residue was purified on a silica gel column using a 5:4 v/v mixture of petroleum ether (b.p. 40°-60° C.) and methylene chloride as eluant.

A mixture of the ethyl 4-bromomethyl-3-chlorocinnamate thus obtained (1.8 g.) and triethyl phosphite (10 ml.) was heated at 150° C. for 3 hours, the excess of triethyl phosphite was removed by evaporation and the residue was crystallised from petroleum ether (b.p. 80°-100° C). There was thus obtained ethyl 3-chloro-4-(diethoxyphosphonylmethyl)cinnamate, m.p. 88°-90° C.

2-p-[5-(6-Methoxy-2-p-methoxyphenylnaphth-1-yl)pentyl]phenylacetic acid and its (1RS,2RS)-1,2,3,4-tetrahydro derivative A 1.8 molar solution of diisobutylaluminium hydride in toluene (27 ml.) was added dropwise to a stirred solution of ethyl p-bromomethylphenylacetate (4.0 g.; prepared by bromination of ethyl p-tolylacetate with N-bromosuccinimide in carbon tetrachloride solution) in toluene (200 ml.) which was maintained under an atmosphere of argon, and the mixture was stirred for 30 minutes and then poured onto ice-water. The mixture was extracted three times with ethyl acetate (60 ml. each time) and the combined extracts were washed with water, dried and evaporated to dryness. The residue was purified by chromatography on a silica gel column using a 1:1 v/v mixture of diethyl ether and petroleum ether (b.p. 40°-60° C.) as eluant.

Phosphoryl chloride (0.01 ml.) and then dihydropyran (1.4 g.) were successively and dropwise added to a solution of the 2-(p-bromomethylphenyl)ethanol thus obtained (2.7 g.) in methylene chloride (100 ml.) and the mixture was stirred for 1 hour, washed with saturated aqueous sodium bicarbonate solution (50 ml.) and then with water (50 ml.), dried and evaporated to dryness. The residue was purified by chromatography on a silica gel column using a 10:1 v/v mixture of petroleum ether (b.p. 40°-60° C.) and diethyl ether as eluant.

A mixture of the 2-(p-bromomethylphenyl)ethyl tetrahydropyranyl ether thus obtained (3.0 g.) and triethyl phosphite (2.5 g.) was heated at 110° C. for 2 hours, the excess of triethyl phosphite was removed by passing a stream of argon through the hot mixture, and the residue was purified by chromatography on a silica gel column using diethyl ether as eluant.

The diethyl p-(2-tetrahydropyranyloxyethyl)phenylmethylphosphonate thus obtained was reacted with 4-[(1RS, 2RS)-6-methoxy-2-p-methoxyphenyl1,2,3,4-tetrahydronaphth-1-yl]butyraldehyde and the olefinic double bond was hydrogenated by similar processes to those described above, and the tetrahydropyranyl group was removed by acidic hydrolysis by a similar process to that described in the 5th paragraph of Example 2. There was thus obtained 2-p-{5-[(1RS, 2RS)-6-methoxy-2-p-methoxyphenyl1,2,3,4-tetrahydronaphth-1- yl]pentyl}phenylethanol.

Jones' reagent (0.54 ml. of a 1.78 molar solution of chromium trioxide in aqueous sulphuric acid) was added dropwise to a stirred solution of the above phenylethanol (0.2 g.) in acetone (10 ml.) which was cooled to −20° C., and the mixture was kept at −15° C. for 16 hours. Methanol (2 ml.) was added, the mixture was allowed to warm up to laboratory temperature and was then evaporated to dryness, and the residue was partitioned between ethyl acetate and aqueous 2N-hydrochloric acid. The organic layer was washed with water, dried and evaporated to dryness and there was thus obtained 2-p-{5[(1RS,2RS)-6-methoxy-2-p-methoxyphenyl-1,2,3,4-tetrahydronapth-1-yl]pentyl} phenylacetic acid.

This was reacted with 2,3-dichloro-5,6-dicyano-1,4-benzoquinone by a similar process to that described in the penultimate paragraph of Example 2, and there was thus obtained 2-p-[5-(6-methoxy-2-p-methoxyphenyl-indanapth-1-yl)pentyl]phenylacetic acid.

2-p-[6-(6-Methoxy-2-p-methoxyphenylnaphth-1-yl)hex-yl]phenylacetic acid and its
(1RS,2RS)-1,2,3,4-tetrahydro derivative This was obtained by a similar process to that described in the last paragraph above, except that 5-[(1RS,2RS)-6-methoxy-2-p-methoxyphenyl-1,2,3,4-tet-rahy dronapth-1-yl)pentanal was used in place of the corresponding butyraldehyde. The pentanal itself was obtained by a similar process to that described in Example 2 except that pent-4-ynyl tetrahydropyranyl ether was used in place of propargyl tetrahydropyranyl ether.

EXAMPLE 4

The process described in Example 1 was repeated using 10-[(1RS, 2RS)-5-methoxy-2-p-methoxyphenylin-dan-1-yl]decanoic acid and n-hexylamine as starting materials. There was thus obtained as an oil N-n-hexyl-10-[(1RS, 2RS)-5-hydroxy-2-p-hydroxyphenylindan-1-yl]decanamide, the structure of which was confirmed by proton magnetic resonance and mass spectroscopy.

The decanoic acid used as starting material was obtained as follows:

A Grignard solution was prepared from 10-(dimeth-yl-t-butylsilyloxy)decyl bromide (3.5 g.), magnesium turnings (0.24 g.) and tetrahydrofuran (25 ml.) and was heated under reflux for 1 hour and then stirred and cooled to laboratory temperature. A solution of 5-methoxy-2-p-methoxyphenylindan-1-one (1.4 g., prepared as described in the Journal of Organic Chemistry, 1946, 11, 44) in tetrahydrofuran (5 ml.) was added during 3 minutes and the mixture was stirred for 1 hour and then poured into saturated aqueous ammonium chloride solution (50 ml.). The mixture was extracted twice with diethyl ether (30 ml. each time ) and the extract was dried and evaporated to dryness. The residue was purified by chromatography on a silica gel column using a 10:3 v/v mixture of petroleum ether (b.p. 40°–60° C.) and diethyl ether as eluant.

A solution of the 1-(10-dimethyl-t-butylsilylox-ydecyl)-5-methoxy-2-p-methoxyphenylindan-1-ol thus obtained (0.8 g.) in ethyl acetate (15 ml.) was stirred at laboratory temperature under an atmosphere of hydrogen in the presence of a 10% palladium-on-charcoal catalyst (0.3 g.) for one hour. The mixture was filtered and the filtrate was evaporated to dryness. Methanolic 20% hydrogen chloride solution (2 ml.) was added to the residue and the mixture was heated at 50° C. for 5 minutes and then evaporated to dryness under reduced pressure. Sufficient Jones' reagent (8N-chromic acid solution) was added to a solution of the 10-(5- methoxy-2-p-methoxyphenylindan-1-yl)decanol thus obtained (0.7 g.) in acetone (10 ml.) which was cooled to −20° C. until a green colour persisted. The liquid was decanted off the solid, the solid was washed with acetone and the combined acetone solutions were stirred with solid sodium bicarbonate and then filtered. The filtrate was evaporated to dryness and the residue was purified by chromatography on a silica gel column using a 100:3 v/v mixture of methylene chloride and methanol as eluant. There was thus obtained as an oil 10-[(1RS, 2RS)-5-methoxy-2-p-methoxyphenylindan-1-yl]decanoic acid.

EXAMPLE 5

The process described in Example 4 was repeated using the appropriate omega-indanylalkanoic or inda-nyl-alkyl-phenylene-alkanoic acid derivative and the appropriate amine as starting materials. There were thus obtained as oils the compounds described in the following table, the structures of which were confirmed by proton magnetic resonance and mass spectroscopy.

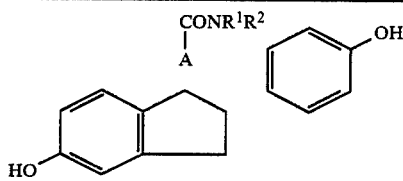

| A | $R^1$ | $R^2$ |
|---|---|---|
| —(CH$_2$)$_9$— | n-hexyl | methyl |
| —(CH$_2$)$_{10}$— | n-butyl | methyl |
| —(CH$_2$)$_{10}$— | 1H,1H—heptafluorobutyl | H |
| —(CH$_2$)$_{10}$— | 1H,1H—heptafluorobutyl | methyl |
| —(CH$_2$)$_{11}$— | n-butyl | methyl |
| —(CH$_2$)$_5$—C$_6$H$_4$—4-(CH$_2$)$_2$— | n-butyl | methyl |
| —(CH$_2$)$_5$—C$_6$H$_4$—4-(CH$_2$)$_2$— | 1H,1H—heptafluorobutyl | H |
| —(CH$_2$)$_5$—C$_6$H$_4$—4-(CH$_2$)$_2$— | 1H,1H—heptafluorobutyl | methyl |

The starting materials for the preparation of compounds wherein A is (CH$_2$)$_{10}$ or (CH$_2$)$_{11}$ were prepared from the decanol used as intermediate in the preparation of compounds wherein A is (CH$_2$)$_9$ (Example 4) as follows:

(a) A solution of tri-phenylphosphine (1.7 g.) in methylene chloride (20 ml.) was added dropwise to a rapidly stirred solution of 10-[(1RS, 2RS)-5-methoxy-2-p-methoxyphenylindan-1-yl]decanol (2.1 g; Example 4) and carbon tetrabromide (2.2 g.) in methylene chloride (75 ml.) and the mixture was stirred for 1 hour and then evaporated to dryness. The residue was stirred with diethyl ether, the mixture was filtered and the filtrate was evaporated to dryness. The residue was purified by chromatography on a silica gel column using a 3:1 v/v mixture of diethyl ether and petroleum ether (b.p. 40°–60° C.) as eluant.

A solution of the 10-[(1RS, 2RS)-5-methoxy-2-p-methoxyphenylindan-1-yl]decyl bromide thus obtained (1.0 g.) in dimethyl sulphoxide (5 ml.) was added dropwise to a stirred suspension of potassium cyanide (0.17 g.) in dimethyl sulphoxide (5 ml.) which was heated at 90° C., and the mixture was stirred at that temperature for 1 hour. Further potassium cyanide (0.17 g.) was added and the mixture was stirred at 90° C. for 1 hour and then evaporated to dryness. The residue was partitioned between water and ethyl acetate and the organic layer was separated, dried and evaporated to dryness. The residue was purified by chromatography on a short silica gel column using diethyl ether as eluant.

A solution of the 10-[(1RS, 2RS)-5-methoxy-2-p-methoxyphenylindan-1-yl]decyl cyanide thus obtained (0.71 g.) in ethanol (25 ml.) was added to a solution of potassium hydroxide (0.6 g.) in water (5 ml.) and the mixture was heated under reflux for 24 hours, cooled and extracted with diethyl ether. The aqueous solution was acidified with concentrated aqueous hydrochloric acid and extracted with diethyl ether, and the extract was dried and evaporated to dryness. The residue was purified by chromatography on a silica gel column using a 100:3 v/v mixture of methylene chloride and methanol as eluant. There was thus obtained 11-[(1RS, 2RS)-5-methoxy-2-p-methoxyphenylindan-1-yl]undecanoic acid.

(b) A solution of diethyl malonate (0.64 g.) in dimethylformamide (10 ml.) was added to a stirred suspension of sodium hydride (0.14 g. of a 50% suspension in mineral oil) in dimethylformamide (10 ml.) which was maintained under an atmosphere of argon, and the mixture was stirred and heated to 50° C. for 5 minutes and then cooled to laboratory temperature. 10-[(1RS, 2RS)-5-Methoxy-2-p-methoxyphenylindan-1yl]decyl bromide (1.2 g.) was added and the mixture was stirred at laboratory temperature for 16 hours and then diluted with water and extracted with diethyl ether. The extract was dried and evaporated to dryness and a solution of the residue (1.47 g.) in ethanol (10 ml.) was added dropwise to a stirred solution of potassium hydroxide (1.4 g.) in water (10 ml.) which was heated under reflux. The mixture was stirred and heated under reflux for 10 minutes, diluted with water and extracted with diethyl ether. The aqueous solution was acidified with concentrated aqueous hydrochloric acid and extracted with diethyl ether, and the extract was dried and evaporated to dryness. There was thus obtained as residue 12-[(1RS, 2RS)-5-methoxy-2-p-hydroxyphenylindan-1-yl]dodecanoic acid.

The starting material for the preparation of compounds wherein A is —$(CH_2)_5C_6H_4$—4—$(CH_2)_2$—was prepared by a similar sequence of processes to that described in Examples 2 and 3, using but-3-ynyl tetrahydropyranyl ether and 5-methoxy-2-p-methoxyphenylindan-1-one as initial starting materials to prepare 4-[(1RS,2RS)-5-methoxy-2-p-methoxyphenylindan1-yl]butyraldehyde by a similar process to that described in Example 2, and converting this via the cinnamate to 3-p-{5-[(1RS,2RS)-5-methoxy-2-p-methoxyphenylindan-1-yl]-pentyl}phenylpropionic acid by a similar process to that described in Example 3.

EXAMPLE 6

The process described in Example 1 was repeated using the appropriate (6-methoxy-2-p-methoxyphenyl-2-methyl-1,2,3,4-tetrahydronaphth-1-yl)alkanoic acid derivative and the appropriate amine as starting materials, and there were thus obtained as oils the compounds described in the following table, the structures of which were confirmed by proton magnetic resonance and mass spectroscopy

| A | $R^1$ | $R^2$ | Isomer |
|---|---|---|---|
| —$(CH_2)_{11}$— | n-butyl | methyl | (Mixed) |
| —$(CH_2)_4$—$C_6H_4$—4-$(CH_2)_2$— | 1H,1H,heptafluorobutyl | methyl | A |
| —$(CH_2)_4$—$C_6H_4$—4-$(CH_2)_2$— | 1H,1H—heptafluorobutyl | methyl | B |

Proton magnetic resonance spectroscopy shows that the first compound in the table is a mixture of (1RS,2RS) and (1RS,2SR) isomers whereas the second and third compounds are pure (1RS,2RS) and (1RS,2SR) isomers which were separated from one another by chromatography on a silica gel column using a 17:3 v/v mixture of toluene and ethyl acetate as eluant.

The starting alkanoic acids were obtained as follows:

A solution of 3,4-dihydro-6-methoxy-2-p-methoxyphenynaphthalen-1(2H)-one (14.4 g.) in tetrahydrofuran (200 ml.) was added to a stirred solution of lithium diisopropylamide in tetrahydrofuran [prepared from n-butyllithium (31 ml. of a 1.6 molar solution in hexane ) and a solution of diisopropylamine (5.1 g.) freshly distilled from potassium hydroxide) in tetrahydrofuran (50 ml.)]which was cooled to −60° C. under an atmosphere of argon. The mixture was stirred at −60° C. for 30 minutes, methyl iodide (7 g.) was added and the mixture was stirred at laboratory temperature for 12 hours and then poured into saturated aqueous ammonium chloride solution (600 ml.). The mixture was extracted three times with ethyl acetate (100 ml. each time) and the combined extracts were washed with water, dried and evaporated to dryness. The residue was purified by chromatography on a silica gel column using a 9:1 v/v mixture of petroleum ether (b.p. 60°-80° C.) and ethyl acetate as eluant. There was thus obtained 3,4-dihydro-6-methoxy-2-p-methoxyphenyl-2-methylnaphthalen-1(2H)-one, m.p. 76°-78° C.

n-Butyllithium (40 ml. of a 1.65 molar solution in hexane) was added dropwise to a stirred solution of propargyl tetrahydropyranyl ether (10 g.) in tetrahydrofuran (200 ml.) which was cooled to 0° C. under an atmosphere of argon, and a solution of the above naphthalenone (9 g.) in tetrahydrofuran (100 ml.) was added. The mixture was stirred at laboratory temperature for 2 hours and then poured into ice-cold, saturated aqueous ammonium chloride solution (300 ml.) The mixture was extracted three times with ethyl acetate (100 ml.) each time) and the combined extracts were washed with water, dried and evaporated to dryness. The residue was stirred with petroleum ether (b.p. 60°-80° C.) and the mixture was filtered. There was thus obtained 1,2,3,4-tetrahydro-6-methoxy-2-p-methoxyphenyl-2-methyl1-(3-tetrahydropyranyloxypropynyl)naphth-1-ol.

The above compound was converted to 3-[6-methoxy-2-p-methoxyphenyl-2-methyl 1,2,3,4-tetrahydro-naphth-1-yl]propionaldehyde by the successive steps of hydrogenation, acidic hydrolysis and oxidation with pyridinium chlorochromate in a similar manner to to that described in Example 2. This aldehyde was then either reacted with (8-carboxyoctyl)triphenylphosphonium bromide and the product hydrogenated by similar processes to those described in Example 2 to give 12-(6-methoxy-6-p-methoxyphenyl-2-methyl-1,2,3,4-tetrahydronaphth-1-yl)dodecanoic acid, or it was reacted with ethyl p-(diethoxyphosphonylmethyl)-cinnamate and the product hydrogenated by similar processes to those described in Example 3 to give 3-p-[4-(6-methoxy-2-p-methoxyphenyl-2-methyl-1,2,3,4-tetrahydronaphth-1-yl)butyl]-phenylpropionic acid. Both these acids are mixtures of (1RS, 2RS) and (1RS,2SR) isomers.

Example 7

Heptanethiol (1.0 g.) was added to a suspension of sodium hydride (0.36 g. of a 50% dispersion in mineral oil from which the oil had been washed with petroleum ether) in a mixture of tetrahydrofuran (40 ml.) and dimethylformamide (20 ml.), and the mixture was stirred at laboratory temperature for 2 hours and then at 40° C. for 3 hours. One quarter of the resulting solution (15 ml.) was added to a solution of (1RS, 2RS)-1-(9-mesyloxynonyl)-6-methoxy-2-p-methoxyphenyl-1,2,3,4-tetrahydronaphthalene (0.5 g.) in tetrahydrofuran (40 ml.) and the mixture was stirred at laboratory temperature for 16 hours, diluted with water (30 ml.) and extracted three times with ethyl acetate (20 ml. each time). The combined extracts were dried and evaporated to dryness and the residue was purified by chromatography on a silica gel column using a 10:1 v/v mixture of toluene and ethyl acetate as eluant. A solution of boron tribromide (1.6 g.) in methylene chloride (3 ml.) was added to a stirred solution of the (1RS, 2RS)-1-(9-n-heptylthiononyl)-6-methoxy-2-p-methoxyphenyl-1,2,3,4-tetrahydronaphthalene thus obtained (0.06 g.) in methylene chloride (5 ml.) which was cooled to −70° C. under an atmosphere of argon, and the mixture was allowed to warm up to 0° C., stirred at that temperature for 3 hours and then poured onto ice (20 g.). The mixture was extracted three times with methylene chloride (10 ml. each time) and the combined extracts were washed with water, dried and evaporated to dryness. The residue was purified by chromatography on a silica gel column using a 20:1 v/v mixture of toluene and ethyl acetate as eluant. There was thus obtained (1RS, 2RS)-1-(9-n-heptylthiononyl)-2-p-hydroxyphenyl-1,2,3,4-tetrahydronaphth-6-ol, the structure of which was confirmed by proton magnetic resonance and mass spectroscopy.

The (1RS, 2RS)-1-(9-mesyloxynonyl)-6-methoxy-2-p-methoxyphenyl-1,2,3,4-tetrahydronaphthalene used as starting material was obtained as follows:

A solution of (1RS, 2RS)-9-(6-methoxy-2-p-methoxyphenyl-1,2,3,4-tetrahydronaphth-1-yl)nonanoic acid (0.58 g.; Example 2 using (5-carboxypentyl)triphenylphosphonium bromide as reactant) in diethyl ether (10 ml.) was added to a stirred suspension of lithium aluminium hydride (0.26 g.) in diethyl ether (15 ml.) which was maintained under an atmosphere of argon, and the mixture was stirred for 30 minutes. Water (0.26 ml.), aqueous 15% sodium hydroxide solution (0.26 ml.) and further water (0.78 ml.) were successively added dropwise, and the mixture was filtered. The filtrate was dried and evaporated to dryness and the residual (1RS, 2RS)-9-(6-methoxy-2-p-methoxyphenyl-1,2,3,4-tetrahydronaphth-1-yl)nonanol (0.5 g.) was dissolved in methylene chloride (10 ml.). The stirred solution was cooled to 5° C. and pyridine (0.09 g.) and methanesulphonyl chloride (mesyl chloride; 0.21 g.) were successively added. The mixture was allowed to warm up to laboratory temperature and was stirred for 16 hours. Aqueous 2N-hydrochloric acid (15 ml.) was added, the mixture was extracted three times with methylene chloride (15 ml. each time) and the combined extracts were dried and evaporated to dryness. The residue was purified by chromatography on a silica gel column using a 10:1 v/v mixture of toluene and ethyl acetate as eluant and there was thus obtained (1RS, 2RS)-1-(9-mesyloxynonyl)-6-methoxy-2-p-methoxyphenyl-1,2,3,4-tetrahydronaphthalene.

Example 8

The process described in Example 7 was repeated using the appropriate 1-omega-mesyloxyhydrocarbyl-naphthalene or indane derivative and the appropriate alkanethiol as starting materials. There were thus obtained as oils the compounds described in the following tables, the structures of all of which were confirmed by proton magnetic resonance and mass spectroscopy:

TABLE I

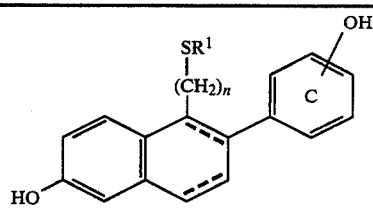

| n | R¹ | Optional Double Bonds | Position of OH in Ring C | Substituent in Ring C |
|---|---|---|---|---|
| 9 | n-heptyl | absent⁺ | 4- | — |
| 9 | n-heptyl | present | 4- | — |
| 10 | n-hexyl | absent | 4- | — |
| 10 | n-hexyl | present* | 4- | — |
| 10 | n-hexyl | absent | 4- | 2-methyl |
| 10 | n-hexyl | absent | 4- | 2-ethyl |
| 10 | n-hexyl | absent | 4- | 3-methyl |
| 10 | n-hexyl | present* | 4- | 3-methyl |
| 10 | n-hexyl | absent | 4- | 2,5-dimethyl |
| 10 | n-hexyl | absent | 3- | — |
| 11 | n-pentyl | absent | 4- | — |
| 11 | 4-chlorophenyl | absent | 4- | — |
| 11 | 4-chlorophenyl | present | 4- | — |

Note to Table 1
*These naphthalene derivatives (double bond present) were prepared by aromatisation of the corresponding tetrahydronaphthalene (double bond absent) with 2,3-dichloro-5,6-dicyano-1,4-benzoquinone by a similar process to that described in the penultimate paragraph of Example 2.
⁺all tetrahydronaphthalenes apart fron the one marked ⁺ are (1RS,2RS)-isomers. The one marked ⁺ is a (1RS,2SR)-isomer, the starting material for which is described below.

Preparation of starting materials for compounds of Table 1

The mesyloxy compounds used as starting materials were all prepared by a similar process to that described in Example 7 by mesylation of the corresponding carbinol. The carbinol starting materials for compounds wherein ring C bears a hydroxy group in the 4-position and no further substituent were obtained by a similar process to that described in Example 7, by reduction of the corresponding carboxylic acid and mesylation of the carbinol thus obtained. The carboxylic acids themselves were obtained as described in Example 2 using the appropriate omega-carboxyalkyltriphenylphosphonium bromide.

The carbinol intermediates for compounds wherein ring C is other than 4-hydroxyphenyl were prepared by a process exemplified by the following preparation of 10-[(1RS, 2RS)-1,2,3,4-tetrahydro-6-methoxy-2-m-methoxy-phenylnaphth-1-yl]decanol:

A solution of m-methoxyphenylacetic acid (1.33 g.) in tetrahydrofuran (10 ml.) was added to a stirred solution of lithium diisopropylamide, generated from diisopropylamine (2.1 ml.) and n-butyllithium (9.23 ml. of a 1.6 molar solution in hexane) in tetrahydrofuran (15 ml.), which was cooled to $-70°$ C.; and the mixture was allowed to warm up to laboratory temperature, stirred at that temperature for 30 minutes and cooled to $-70°$ C. A solution of 2-m-methoxyphenylethyl methanesulphonate (1.9 g.) in tetrahydrofuran (5 ml.) was added, the mixture was allowed to warm up to laboratory temperature and was stirred at that temperature for 18 hours, and water (50 ml.) was added. The mixture was washed with diethyl ether, acidified with aqueous 6N-hydrochloric acid and extracted three times with ethyl acetate (50 ml. each time). The combined extracts were washed with water, dried and evaporated to dryness and there was thus obtained as residue 2,4-bis-(m-methoxyphenyl)butyric acid.

Dimethylformamide (0.1 ml.) and then oxalyl chloride (1 ml.) were successively added to a solution of the above acid (2.1 g.) in toluene (20 ml.) and the mixture was stirred at laboratory temperature for 1 hour and then evaporated to dryness. The residue was dissolved in methylene chloride (30 ml.) the solution was cooled to $-25°$ C., stannic chloride (0.95 ml.) was added and the mixture was stirred for 90 minutes. Water (20 ml.) was added and the mixture was extracted three times with methylene chloride (20 ml. each time). The combined extracts were washed with saturated aqueous sodium bicarbonate solution, dried and evaporated to dryness and there was thus obtained as residual oil 3,4-dihydro-6-methoxy-2-m-methoxyphenylnaphthalen1(2H)-one.

A solution of the above compound (0.282 g.) in tetrahydrofuran (2 ml.) was added to a boiling mixture of 10-(dimethyl-t-butylsilyloxy)dec-1-yne (0.8 g., prepared as described below) in tetrahydrofuran (10 ml.) and methyl magnesium chloride (0.69 ml. of a 2.9 molar solution in tetrahydrofuran) which had previously been heated under reflux for 1 hour under an atmosphere of argon, and the mixture was heated under reflux for 30 minutes, cooled and poured into ice-cold saturated aqueous ammonium chloride solution (10 ml.). The mixture was extracted three times with ethyl acetate (20 ml. each time) and the combined extracts were washed with water, dried and evaporated to dryness. There was thus obtained as residual oil 1-(10-dimethyl-t-butyl-silyloxy- dec-1-ynyl)-6-methoxy-2-m-methoxyphenyl-1,2,3,4-tetrahydronaphth-1-ol.

A solution of the above compound (0.3 g.) in ethyl acetate (10 ml.) was stirred with a 10% palladium-on charcoal catalyst (0.1 g.) under an atmosphere of hydrogen for 18 hours, filtered and the filtrate was evaporated to dryness. A mixture of the residue (0.346 g.), acetic acid (6.7 ml.), water (3.3 ml.) and tetrahydrofuran (3 ml.) was stirred at laboratory temperature for 18 hours and then evaporated to dryness and the residue was purified by chromatography on a silica gel column using a 10:1 v/v mixture of toluene and ethyl acetate as eluant. There was thus obtained 10-[(1RS,2RS)-6-methoxy-2-m-methoxyphenyl-1,2,3,4-tetrahydronaphth-1-yl]decanol.

Other related compounds were obtained by using the appropriate methoxyphenylacetic acid as original starting material in place of m-methoxyphenylacetic acid.

The 10-(dimethyl-t-butylsilyloxy)dec-1-yne was obtained as follows:

A solution of dimethyl-t-butylsilyl chloride (18 g.) in tetrahydrofuran (50 ml.) was added dropwise to a stirred solution of 8-bromooctanol (20 g.) and imidazole (14.2 g.) in tetrahydrofuran (100 ml.) and the mixture was stirred at laboratory temperature for 3 hours, diluted with diethyl ether (200 ml.) and filtered. The filtrate was evaporated to dryness and the residue was purified by chromatography on a silica gel column using petroleum ether (b.p. 60°-80° C.) as eluant. A solution of the 8-(dimethyl-t-butylsilyloxy)octyl bromide thus obtained (6.46 g.) in dimethyl sulphoxide (2 ml.) was added to a stirred suspension of lithium acetylide-ethylenediamine complex (2.02 g.) in dimethylsulphoxide (30 ml) which was cooled to 10° C.; and the mixture was stirred for 18 hours and then poured into ice-water (150 ml.). The mixture was extracted three times with petroleum ether (b.p. 60°–80° C.; 30 ml. each time) and the combined extracts were washed with water (10 ml.), dried and evaporated to dryness. The residue was purified by chromatography on a silica gel column using a 5:1 v/v mixture of cyclohexane and diethyl ether as eluant. There was thus obtained 10-(dimethyl-t-butylsilyloxy)dec-1-yne.

Preparation of
9-[1RS,2SR)-6-methoxy-2-p-methoxyphenyl-1,2,3,4-tetrahydronaphth-1-yl]nonanol A solution of 1-cyano-4-methoxybenzocyclobutene (7.5 g.; described in the Journal of the American Chemical Society, 1976, 98, 8185) and p-methoxystyrene (11.1 g.) in o-dichlorobenzene (40 ml.) was heated under reflux for 30 minutes under an atmosphere of argon and then evaporated to dryness, and the residue was purified by chromatography on a silica gel column using a 20:1 v/v mixture of toluene and ethyl acetate as eluant. A mixture of a solution of the residue (12.0 g.) in toluene (200 ml.), a solution of sodium hydroxide (20 g.) in water (200 ml.) and 40% w/v aqueous tetrabutylammonium hydroxide solution (1 ml.) was stirred vigorously under an atmosphere of argon at laboratory temperature for 12 hours and the layers were then separated. The aqueous layer was extracted twice with diethyl ether (100 ml. each time) and the combined organic solutions were washed with water, dried and evaporated to dryness. There was thus obtained as residue (1RS,2SR)-1-cyano-1,2,3,4-tetrahydro-2-p-methoxyphenylnaphthalene, m.p. 126°–131° C.

Diisobutylaluminium hydride (5.8 ml. of a 1.8 molar solution in toluene) was added to a stirred solution of the above nitrile (0.75 g.) in toluene (30 ml.) under an atmosphere of argon, and the mixture was stirred at laboratory temperature for 1 hour. Methanol (10 ml.) and aqueous 2N-hydrochloric acid (20 ml.) were successively added, the mixture was stirred for 30 minutes and the layers were separated. The aqueous layer was extracted twice with diethyl ether (30 ml. each time) and the combined organic solutions were washed with water, dried and evaporated to dryness. The residue was purified by chromatography on a silica gel column using a 7:3 v/v mixture of petroleum ether (b.p. 40°-60° C.) and diethyl ether as eluant. There was thus obtained (1RS, 2SR)-6-methoxy-2-p-methoxyphenyl-1,2,3,4-tetrahydronaphth-1-aldehyde.

The above aldehyde was reacted with (7-carboxyheptyl)triphenylphosphonium bromide, and the nonenoic acid thus obtained was hydrogenated by a similar process to that described in Example 2. The nonanoic acid thus obtained was reduced with lithium aluminium hydride by a similar process to that described in Example 7.

TABLE 2

(1RS, 2RS) - Isomers

| p | q | $R^1$ | Position of $(CH_2)_qSR^1$ |
|---|---|---|---|
| 3 | 2 | n-octyl | 4- |
| 3 | 2 | n-octyl | 3- |
| 3 | 3 | n-heptyl | 4- |
| 4 | 1 | n-heptyl | 4- |
| 4 | 2 | n-hexyl | 4- |
| 4 | 2 | 4,4,5,5,5-pentafluoropentyl | 4- |
| 4 | 2 | 4,4,4-trifluorobutyl | 4- |
| 4 | 2 | benzyl | 4- |
| 4 | 2 | 4-methylbenzyl | 4- |
| 4 | 2 | 3,4-dichlorobenzyl | 4- |
| 4 | 2 | 4-chlorobenzyl | 4- |
| 4 | 2 | 4-phenylbenzyl | 4- |
| 4 | 2 | 4-methylthiobenzyl | 4- |
| 4 | 2 | 4-trifluoromethylbenzyl | 4- |
| 4 | 2 | 4-cyanobenzyl | 4- |
| 4 | 2 | phenethyl | 4- |
| 4 | 2 | 2-(4-chlorophenyl)ethyl | 4- |
| 4 | 2 | 2-(4-fluorophenyl)ethyl | 4- |
| 4 | 2 | n-hexyl | 3- |
| 4 | 3 | n-pentyl | 4- |
| 4 | 3 | 4-chlorobenzyl | 4- |
| 4 | 3 | n-hexyl | 3- |
| 5 | 1 | n-hexyl | 4- |
| 5 | 2 | n-hexyl | 4- |
| 5 | 2 | 4,4,5,5,5-pentafluoropentyl | 4- |
| 5 | 2 | 4-chlorobenzyl | 4- |
| 5 | 2 | n-hexyl | 3- |
| 5 | 3 | n-pentyl | 4- |
| 5 | 3 | 4-chlorobenzyl | 3- |
| 6 | 2 | 4-chlorobenzyl | 4- |

Preparation of starting materials for compounds of Table 2

The mesyloxy compounds used as starting materials were all prepared by a similar process to that described in Example 7 by mesylation of the corresponding carbinol, and the carbinols themselves were obtained by the reduction of the corresponding carboxylic acids or esters of said acids by a similar process to that described in the second part of Example 7.

Carbinols which produce compounds wherein p is 4 or 5, q is 3 and the —(CH2)q— linkage is in the 3 or 4-position were prepared by lithium aluminium hydride reduction of the ethyl esters of the phenylpropionic acids described in Example 3 (the preparation of these ethyl esters is described in Example 3 but the esters were then hydrolysed without being characterised). A similar process was used to produce carbinols wherein p is 3 and q is 3, tetrahydronaphth-1-ylacetaldehyde used as initial starting material being described below.

Carbinols wherein p is 5 or 6, q is 2 and the —(CH$_2$)$_q$— linkage is in the 4-position are described in Example 3. Carbinols wherein p is 3 or 4, q is 2 and the —(CH$_2$)$_q$— linkage is in the 4-position were similarly obtained from corresponding tetrahydronaphth-1-yl-acetaldehyde (described below) or propionaldehyde (described in Example 2). The corresponding compounds wherein the —(CH$_2$)$_q$— linkage is in the 3-position were similarly obtained using ethyl m-bromomethylphenylacetate as initial starting material in place of the corresponding p-compound.

where P is 4,5 or 6,9 is 1 and the (CH$_2$)$_q$— linkage is in the 4-position were obtained by hydrolysis of the corresponding ethyl benzoates, which themselves were obtained by a similar process to that described in Example 3 using ethyl p-(diethoxyphosphonylmethyl)benzoate in place of the corresponding cinnamate.

Preparation of 2-[(1RS,2RS)-6-methoxy-2-p methoxyphenyl-1,2,3,4-tetrahydronaphth-1-yl]-acetaldehyde A stirred mixture of 3,4-dihydro-6-methoxy-2-p-methoxyphenylnaphthalen-1(2H)-one (10 g.), ethyl bromoacetate (17.8 g.), zinc (11.6 g.), benzene (200 ml.) and one crystal of iodine was heated under reflux under an atmosphere of argon for 10 minutes, allowed to continue to boil until the exothermic reaction subsided, heated again under reflux for a further 10 minutes and then cooled to laboratory temperature. Saturated aqueous ammonium chloride solution (100 ml.) was added, the mixture was filtered and the organic layer of the filtrate was separated, dried and evaporated to dryness. A 10% palladium-on-charcoal catalyst (2 g.) was added to a solution of the residue (13.1 g.) in ethyl acetate (300 ml.) and the mixture was stirred under an atmosphere of hydrogen for 3 hours, filtered, and rehydrogenated with fresh catalyst (2 g.) for 18 hours. The mixture was filtered, the filtrate was evaporated to dryness and the residue was purified by chromatography on a silica gel column using a 25: 1 v/v mixture of toluene and ethyl acetate. The ethyl [(1RS,2RS)-6-methoxy-2-p-methoxyphenyl-1,2,3,4-tetrahydronaphth-1-yl]acetate thus obtained was reduced with lithium aluminium hydride (4.4 g.) by a similar process to that described in Example 7, and the ethanol thus obtained (m.p. 98°–99° C.) was oxidised with pyridinium chlorochromate (8.6 g.) by a similar process to that described in the 6th paragraph of Example 2. There was thus obtained the desired acetaldehyde, m.p. 101°–103° C.

TABLE 3

(1RS, 2RS) - Isomers

| p | q | $R^1$ | Position of $(CH_2)_qSR^1$ |
|---|---|---|---|
| 4 | 2 | n-hexyl* | 4- |

TABLE 3-continued

[Structure: (1RS, 2RS) - Isomers of tetrahydronaphthalene with (CH2)p-phenol and (CH2)qSR1 substituents, HO- on naphthalene ring]

(1RS, 2RS) - Isomers

| p | q | R¹ | Position of (CH₂)qSR¹ |
|---|---|---|---|
| 4 | 2 | 4,4,5,5,5-pentafluoropentyl | 4- |
| 4 | 2 | benzyl | 4- |
| 4 | 2 | 3,4-dichlorobenzyl | 4- |
| 4 | 2 | 4-chlorobenzyl | 4- |
| 4 | 2 | 4-phenylbenzyl | 4- |
| 4 | 2 | 4-methylthiobenzyl | 4- |
| 4 | 2 | 4-trifluoromethylbenzyl | 4- |
| 4 | 2 | 2-(4-fluorophenyl)ethyl | 4- |
| 4 | 2 | n-hexyl | 3- |
| 4 | 3 | n-hexyl | 3- |
| 5 | 1 | n-hexyl | 4- |
| 5 | 2 | 4,4,5,5,5-pentafluoropentyl | 4- |
| 5 | 2 | n-hexyl | 3- |
| 5 | 3 | 4-chlorobenzyl | 3- |
| 6 | 2 | 4-chlorobenzyl | 4- |

Note to Table 3
*Apart from the compound marked * all (1RS,2SR)-isomers were by- products formed during the preparation of the (1RS,2RS)-isomers described in Table 2 above, and were separated therefrom by chromatography on a silica gel column using mixtures of toluene and ethyl acetate as eluants.

Preparation of starting material for compound marked * in Table 3

The mesyloxy compound used as starting material was prepared by a similar process to that described in Example 7 by mesylation of the corresponding carbinol, and the carbinol itself was prepared as follows:

2-p-4-[(1RS,2SR)-6-methoxy-2-p-methoxyphenyl-1,2,3,4-tetrahydronaphth-1-yl]butyl phenylethanol n-Butyllithium (5.5 ml. of a 1.5 molar solution in hexane) was added dropwise to a stirred suspension of (methoxymethyl)triphenylphosphonium chloride (3.1 g.) in tetrahydrofuran (30 ml.) which was maintained at −40° C. under an atmosphere of argon. A solution of (1RS, 2SR)-6-methoxy-2-p-methoxyphenyl-1,2,3,4-tetrahydronaphth-1-aldehyde (0.9 g.); prepared as described after Table 1 above) in tetrahydrofuran (10 ml) was added dropwise at −40° C. and the mixture was stirred at that temperature for 18 hours and then allowed to warm up to laboratory temperature. Saturated aqueous ammonium chloride solution (20 ml.) was added and the mixture was extracted three times with diethyl ether (30 ml. each time). The combined extracts were washed with water and dried, and perchloric acid (1 ml.) was added. The mixture was stirred at laboratory temperature for 4 hours, water (20 ml.) was added and the ethereal layer was separated, dried and evaporated to dryness. The residue was purified by chromatography on a silica gel column using toluene as eluant, and there was thus obtained 2-[(1RS,2SR)-6-methoxy-2-p-methoxyphenyl-1,2,3,4-tetrahydronaphth-1-yl]-acetaldehyde.

Triphenylphosphine (8.4 g.) and potassium carbonate (4.9 g.) were added to a stirred solution of 2-[p-(2-bromoethyl)phenyl]ethyl tetrahydropyranyl ether (10 g.) in acetonitrile (200 ml.) and the mixture was heated under reflux for 36 hours, cooled and filtered. The filtrate was evaporated to dryness and the residue was purified by chromatography on a silica gel column using a 10:1 v/v mixture of methylene chloride and methanol as eluant. n-Butyllithium (1.2 ml. of a 1.5 molar solution in hexane) was added to a stirred solution of the phenethyltriphenylphosphonium bromide thus obtained (1.1 g.) in tetrahydrofuran (5 ml.) which was maintained at −40° C. under an atmosphere of argon, and a solution of the above acetaldehyde (0.2 g.) in tetrahydrofuran (5 ml.) was added. The reaction mixture was stirred at −40° C. for 18 hours, allowed to warm up to laboratory temperature and saturated aqueous ammonium chloride solution (10 ml.) was added. The mixture was extracted three times with diethyl ether (10 ml. each time) and the combined extracts were washed with water, dried and evaporated to dryness. The residue was purified by chromatography on a silica gel column using a 3:1 v/v mixture of petroleum ether (b.p. 40°-60° C.) and diethyl ether as eluant. The product thus obtained was hydrogenated over a palladium-on-charcoal catalyst by a similar process to that described in the second part of Example 3, and the tetrahydropyranyl group was removed by acidic hydrolysis by a similar process to that described in the fifth paragraph of Example 2. There was thus obtained as an oil 2-p-{4-[(1RS, 2SR)-6-methoxy-2-p-methoxyphenyl-1,2,3,4-tetrahydronaphth-1-yl]butyl}(phenylethanol.

TABLE 4

[Structure: naphthalene derivative with (CH2)qSR1 on phenyl, (CH2)p chain, phenol-OH, and HO- on naphthalene]

| p | q | R¹ | Position of (CH₂)qSR¹ |
|---|---|---|---|
| 3 | 2 | n-octyl | 4- |
| 3 | 2 | n-octyl | 3- |
| 3 | 3 | n-heptyl | 4- |
| 4 | 3 | n-pentyl* | 4- |
| 5 | 2 | n-hexyl* | 4- |
| 5 | 2 | 4,4,5,5,5-pentafluoropentyl | 4- |
| 5 | 2 | 4-chlorobenzyl | 4- |
| 5 | 2 | n-hexyl | 3- |
| 5 | 3 | n-pentyl* | 4- |
| 6 | 2 | 4-chlorobenzyl | 4- |

Note to TABLE 4
*The three compounds marked * were obtained as described in Example 7 from the mesyloxy compound, the intermediate carbinols being obtained from the carboxylic acids which themselves were obtained by aromatisation of the (1RS,2RS)—tetrahydronaphthalene derivatives described as intermediates for preparation of compounds described in TABLE 2. The aromatisation was carried out using 2,3-dichloro-5,6-dicyano-1,4-benzoquinone by a similar process to that described in the penultimate paragraph of Example 2.

The other compounds described in Table 4 were obtained by the aromatisation as described above of the corresponding (1RS, 2RS)-tetrahyronaphthalene derivatives actually described in Table 2 above.

TABLE 5

[Structure: indane with SR¹ group at position 1 (with A linker), R¹⁴ at position 2, 4-hydroxyphenyl at position 2, and HO- on the aromatic ring]

| A | R¹ | R¹⁴ | Substituted in Ring C |
|---|---|---|---|
| —(CH$_2$)$_{10}$— | n-hexyl | H | — |
| —(CH$_2$)$_{11}$— | n-hexyl | H | — |
| —(CH$_2$)$_{11}$— | n-pentyl | H | — |
| —(CH$_2$)$_{11}$— | n-butyl | H | — |
| —(CH$_2$)$_4$—C$_6$H$_4$—4-(CH$_2$)$_2$— | n-hexyl | H | — |
| —(CH$_2$)$_{10}$— | n-hexyl | methyl | — |
| —(CH$_2$)$_{11}$— | n-pentyl | methyl | — |
| —(CH$_2$)$_4$—C$_6$H$_4$—4-(CH$_2$)$_2$— | n-heptyl | methyl | — |
| —(CH$_2$)$_4$—C$_6$H$_4$—4-(CH$_2$)$_2$— | n-hexyl | methyl | — |
| —(CH$_2$)$_4$—C$_6$H$_4$—4-(CH$_2$)$_2$— | n-pentyl | methyl | — |
| —(CH$_2$)$_4$—C$_6$H$_4$—4-(CH$_2$)$_3$— | n-hexyl | methyl | — |
| —(CH$_2$)$_4$—C$_6$H$_4$—4-(CH$_2$)$_3$— | n-pentyl | methyl | — |
| —(CH$_2$)$_4$—C$_6$H$_4$—4-(CH$_2$)$_2$— | n-hexyl | ethyl | — |
| —(CH$_2$)$_4$—C$_6$H$_4$—4-(CH$_2$)$_2$— | n-pentyl | ethyl | — |
| —(CH$_2$)$_4$—C$_6$H$_4$—4-(CH$_2$)$_3$— | n-pentyl | ethyl | — |
| —(CH$_2$)$_{10}$— | n-hexyl* | H | 2,3,5,6-tetrafluoro |

Note to TABLE 5
*The compound marked * had m.p. 84–86° C.

Preparation of starting materials for compounds of Table 5

The mesyloxy compounds used as starting materials were all prepared by a similar process to that described in Example 7 by mesylation of the corresponding carbinol. The carbinol wherein R¹⁴ is H and A is —(CH$_2$)$_{10}$— is described in Example 4 and the corresponding carbinol wherein R¹⁴ is H and A is —(CH$_2$)$_{11}$— was prepared by a similar process to that described in Example 4 except that 11-(dimethyl-t-butylsilyloxy)undecyl bromide was used in place of the corresponding decyl bromide. The corresponding carbinols wherein R14 is methyl were similarly obtained using 5-methoxy-2-p-methoxy-phenyl-2-methylindan-1-one (the preparation of which is described below) as initial starting material.

The carbinols wherein A is —(CH$_2$)$_4$—C$_6$H$_4$—(CH$_2$)$_2$-were prepared from 3-[(1RS,2RS)-5-methoxy-2-p-methoxyphenylindan-1-yl]propionaldehyde, or from the corresponding 2-methylindanyl or 2-ethylindanyl analogue(the preparation of which is described below) and diethyl p-(2-tetrahydropyranyloxyethyl)phenylmethylphosphonate, followed by hydrogenation of the double bond and acidic hydrolysis of the tetrahydropyranyl group by similar processes to those described in Examples 3 and 2 respectively. The carbinols wherein A is —(CH$_2$)$_4$—C$_6$H$_4$—4—(CH$_2$)$_3$— were obtained from the appropriate indanylpropionaldehyde and ethyl p-(diethoxyphosphonylmethyl)cinnamate, followed by hydrogenation of the double bond and lithium aluminium hydride reduction of the ethyl ester by similar processes to those described in Examples 3 and 7 respectively.

3-[(1RS,2RS)-5-methoxy-2-p-methoxyphenyl-2-methylindan-1-yl]propionaldehyde.

A solution of tetrabutylammonium hydrogen sulphate (3.3 g.) in aqueous N-sodium hydroxide solution (20 ml.) was added to a vigorously stirred mixture of iodomethane (1.25 ml.) and 5-methoxy-2-p-methoxyphenylindan-1-one (2.7 g.) in methylene chloride under an atmosphere of argon, and the mixture was stirred for 40 minutes. The layers were separated, the aqueous layer was extracted twice with methylene chloride (15 ml. each time) and the combined organic solutions were washed with water, dried and evaporated to dryness. The residue was stirred with a 1:1 v/v mixture of toluene and ethyl acetate, the mixture was filtered and the filtrate was evaporated to dryness. The residue was stirred with diethyl ether, the mixture was filtered and there was thus obtained as solid product 5-methoxy-2-p-methoxyphenyl-2-methylindan-5-one, m.p. 106°–108° C.

A solution of the above indanone (4.4 g.) in tetrahydrofuran (20 ml.) was added to a Grignard reagent prepared from 2-(2-bromoethyl)-1,3-dioxan (5.85 g.) and magnesium (0.72 g.) in tetrahydrofuran (10 ml.) and the mixture was stirred for 1 hour and poured into saturated aqueous ammonium chloride solution (50 ml.). The mixture was extracted three times with diethyl ether (50 ml.each time) and the combined extracts were washed with water, dried and evaporated to dryness. A solution of the residue in ethyl acetate (150 ml.) was stirred under an atmosphere of hydrogen in the presence of a 10% palladium-on-charcoal catalyst (1.6 g.) for 4 hours, and then in the presence of a 20% palladium-on-charcoal catalyst (0.8 g.) for 12 hours. The mixture was filtered, the filtrate was evaporated to dryness and the residue was stirred with a 3:1 v/v mixture of petroleum ether (b.p. 40°–60° C.) and diethyl ether. The mixture was filtered and there was thus obtained as solid residue 2-{2-[(1RS,2RS-5-methoxy-2-p-methoxyphenyl-2-methylindan-1-yl]ethyl}-1,3-dioxan, m.p. 86°–88° C.

p-Toluenesulphonic acid (0.09 g.) was added to a solution of the above trimethylene acetal (1.9 g.) in methanol (60 ml.) and the mixture was heated under reflux under an atmosphere of argon for 1 hour and then cooled. Sodium carbonate (4.5 g.) was added, the mixture was evaporated to dryness and the residue was purified by chromatography on a silica gel column using a 1:1 v/v mixture of diethyl ether and petroleum ether (b.p. 40°–60° C.) as eluant. Water (3 ml.) and trifluoroacetic acid (3 ml.) were added to a stirred solution of the dimethyl acetal thus obtained in chloroform (15 ml.) and the mixture was vigorously stirred for 15 minutes. The layers were separated, the aqueous layer was extracted twice with methylene chloride (5 ml. each time) and the combined organic solutions were dried and evaporated to dryness. The residue was purified by chromatography on a silica gel column using a 30:1 v/v mixture of toluene and ethyl acetate as eluant. There was thus obtained as an oil 3-[(1RS,2RS)-5-methoxy-2-p-methoxyphenyl-2-methylindan-1-yl]propionaldehyde.

The corresponding 2-ethylindanyl-propionaldehyde was similarly obtained using iodoethane in place of iodomethane, and the corresponding 2-unsubstituted-indanylpropionaldehyde was similarly obtained using 5-methoxy-2-p-methoxyphenylindan-1-one and the Grignard reagent as starting materials.

Preparation of 10-[(1RS,2RS)-5-methoxy-2-(4-methoxy-2,3,5,6-tetrafluorophenyl)indan-1-yl]decanol A mixture of pentafluorophenylacetic acid (3.5 g.), potassium t-butoxide (5.2 g.) and methanol (50 ml.) was heated under reflux for 16 hours, evaporated to dryness and aqueous 2 N-hydrochloric acid (30 ml.) was added. The mixture was extracted twice with diethyl ether (30 ml. each time) and the combined extracts were dried and evaporated to dryness. The residue was crystallised from petroleum ether (b.p. 60°–80° C.) and there was thus obtained 4-methoxy-2,3,5,6-tetrafluorophenylacetic acid, m.p. 103°–104° C.

The above compound (1.2 g.) was added to a stirred 0.5 molar solution of lithium diisopropylamide in tetrahydrofuran (30 ml.) which was maintained at −50° C. under an atmosphere of argon, and the mixture was allowed to warm up to laboratory temperature and was then recooled to −50° C. m-Methoxybenzyl chloride (1.5 g.) was added and the mixture was allowed to warm up to laboratory temperature and was stirred at that temperature for 3 hours. Aqueous N-hydrochloric acid (50 ml.) and diethyl ether (30 ml.) were added and the organic layer was separated, washed successively twice with aqueous N-sodium hydroxide solution (30 ml. each time) and water (30 ml.), dried and evaporated to dryness. A mixture of the residue and thionyl chloride (20 ml.) was heated under reflux for 15 minutes and then evaporated to dryness, and stannic chloride (1.3 g.) was added to a stirred solution of the residue in dichloroethane (10 ml.). The mixture was stirred at laboratory temperature for 16 hours, aqueous N-hydrochloric acid (20 ml.) and diethyl ether (30 ml.) were added and the organic layer was separated, washed successively with water (20 ml.), aqueous potassium carbonate solution (20 ml.) and water (20 ml.), dried and evaporated to dryness. The residue was crystallised from methanol and there was thus obtained 5-methoxy-2-(4-methoxy-2,3,5,6-tetrafluorophenyl)indan-1-one, m.p. 152°–153° C.

This indanone was reacted with the Grignard reagent prepared from 10-(dimethyl-t-butylsilyloxy)decyl bromide, and the product hydrolysed and hydrogenated as described in Example 4 above, and there was thus obtained 10-[(1RS,2RS)-5-methoxy-2-(4-methoxy-2,3,5,6-tetrafluorophenyl)indan-1-yl]decanol.

TABLE 6

| A | R$^1$ |
|---|---|
| —(CH$_2$)$_{10}$— | n-hexyl |
| —(CH$_2$)$_{10}$— | n-pentyl |
| —(CH$_2$)$_4$—C$_6$H$_4$—4-(CH$_2$)— | n-hexyl |
| —(CH$_2$)$_4$—C$_6$H$_4$—4-(CH$_2$)$_2$— | n-hexyl* |
| —(CH$_2$)$_4$—C$_6$H$_4$—4-(CH$_2$)$_2$ | p-hydroxybenzyl |
| —(CH$_2$)$_4$—C$_6$H$_4$—4-(CH$_2$)$_2$— | 4,4,5,5,5-pentafluoropentyl |
| —(CH$_2$)$_6$—O—(CH$_2$)$_3$— | n-pentyl |

*Note to TABLE 6
The compound marked * was the (1RS,2SR)—isomer isolated as a byproduct from the (1RS,2RS) isomer by chromatography on a silica gel column using a 17:3 v/v mixture of toluene and ethyl acetate as eluant.

Preparation of Starting Materials for Compounds of Table 6

The mesyloxy compounds use as starting materials were all prepared by a similar process to that described in Example 7 by mesylation of the corrresponding carbinol, and the carbinols themselves were obtained by similar methods to those described after Table 1 above or in Example 3 above except that 3,4-dihydro-6-methoxy-2-p-methoxyphenyl-2-methylnaphthalen-1(2H)-one (Example 6) was used as initial starting material for reaction with 10-(dimethyl-t-butylsilyloxy)dec-1-yne or to prepare the intermediate propionaldehyde for reaction with diethyl p-(2-tetrahydropyranyloxyethyl)phenylmethylphosphonate.

The carbinol starting material for the compound wherein A is —(CH$_2$)$_6$—O—(CH$_2$)$_3$— was obtained as follows:

n-Butyllithium (8.4 ml. of a 1.55 molar solution in hexane) was added to a solution of 6-tetrahydropyranyloxyhex-1-yne (2.25 g.) in tetrahydrofuran (25 ml.) at 10° C., the mixture was allowed to warm up to laboratory temperature and was stirred at that temperature for 30 minutes, and was then recooled to 10° C. A solution of 3,4-dihydro-6-methoxy-2-p-methoxyphenyl-2-methylnaphthalen-1(2H)-one (2.0 g.) in tetrahydrofuran (20 ml.) was added dropwise and the mixture was allowed to warm up to laboratory temperature and stirred at that temperature for 30 minutes. Saturated aqueous ammonium chloride solution (50 ml.) was added and the mixture was extracted with ethyl acetate. The extract was dried and evaporated to dryness and the residue was purified by chromatography on a silica gel column using a 3:1 v/v mixture of petroleum ether (b.p. 60°–80° C.) and ethyl acetate as eluant. The product was crystallised from ethanol and there was thus obtained, as a mixture of isomers, 6-methoxy-2-p-methoxyphenyl-2-methyl-1-(6-tetrahydropyranyloxyhex-1-ynyl)-1,2,3,4-tetrahydronaphth-1-ol, m.p. 80°–82° C.

The above naphthol was hydrogenated over a 10% palladium-on-charcoal catalyst and the tetrahydropyranyl protecting group was removed by acidic hydrolysis as described above to give 6-(6-methoxy-2-p-methoxyphenyl-2-methyl-1,2,3,4-tetrahydronaphth-1-yl)hexanol as a mixture of (1RS,2RS) and (1RS,2SR)-isomers, m.p. 76°–83° C.

The hexanol was mesylated with methanesulphonyl chloride in dichloromethane solution, and the mesylate was reacted with propane-1,3-diol in dimethylformamide solution in the presence of sodium hydride. There was thus obtained the desired carbinol starting material.

TABLE 7

| A | R$^1$ | Optional Double Bonds |
|---|---|---|
| —(CH$_2$)$_4$—C$_6$H$_4$—4-CH(CH$_3$)CH$_2$— | n-hexyl | absent |
| —(CH$_2$)$_4$—C$_6$H$_4$—4-C(CH$_3$)$_2$CH$_2$— | n-hexyl | absent |
| —(CH$_2$)$_3$—(2,6-naphthylene)—CH$_2$— | n-heptyl | absent |
| —(CH$_2$)$_3$—(2,6-naphthylene)—CH$_2$— | n-heptyl | present* |
| —(CH$_2$)$_4$—(2,6-naphthylene)—CH$_2$— | n-pentyl | absent |

Note to TABLE 7
*The naphthalene marked * was obtained by aromatisation of the tetrahydronaphthalene described above.

Prepartion of Starting Materials for Compounds of Table 7

The mesyloxy compounds used as starting materials were all prepared by a similar process to that described in Example 7 by mesylation of the corresponding carbinol, and the carbinols themselves were obtained by similar methods to those described above. Thus the first two carbinols were obtained by the reaction of 3-[(1RS,2RS)-6-methoxy-2-p-methoxyphenyl-1,2,3,4-tetrahydronaphth-1-yl]propionaldehyde with, respectively, diethyl p-(1-methyl-2-tetrahydropyranyloxyethyl)phenylmethylphosphonate (prepared from t-butyl p-tolylacetate by al-pha-methylation with methyl iodide in the presence of lithium diisopropylamide, bromination with N-bromosuccinimide, reduction of the ester to the carbinol with diisobutylaluminium hydride, tetrahydropyranylation, and finally reaction with triethyl phosphite, the last four stages being carried out in a similar manner to that described in Example 3) and diethyl p-(1,1-dimethyl-2-tetrahydropyranyloxyethyl) enylmethylphosphonate (also prepared from t-butyl p-tolylacetate, as described above, except that the alphamethylation step was repeated to produce as intermediate t-butyl 2-methyl-2-p-tolylpropionate).

The naphthylene carbinols were obtained by the reaction of 2-[(1RS,2RS)-6-methoxy-2-p-methoxyphenyl-1,2,3,4-tetrahydronaphth-1-yl]acetaldehyde or propionaldehyde with methyl 6-(diethoxyphosphonylmethyl)naphth-2-oate (m.p. 96°–98° C.) by a similar process to that described in Example 3, followed by hydrogenation and reduction with lithium aluminium hydride as described above. The naphthoate itself was obtained from 6-methylnaphth-2-aldehyde (Journal of the American Chemical Society, 1974, 96, 4611) by oxidation with Jones' reagent, esterification with methanol and hydrochloric acid (methyl 6-methylnaphth-2-oate has m.p. 125°–127° C.), bromination with N-bromosuccinimide (methyl 6-bromomethylnaphth-2-oate has m.p. 70°–75° C.) and finally reaction with triethyl phosphite.

EXAMPLE 9

A solution of sodium metaperiodate (0.026 g.) in water (2 ml.) was added to a stirred solution of (1RS,2RS)-1-(9-n-heptylthiononyl)-2-p-hydroxyphenyl-1,2,3,4-tetrahydronaphth-6-ol (Example 7; 0.052 g.) in methanol (20 ml.) and the mixture was stirred for 16 hours. The methanol was removed by evaporation, the residue was extracted three times with ethyl acetate (10 ml. each time) and the combined extracts were washed with water, dried and evaporated to dryness. The residue was purified by chromatography on a silica gel column using a 2:1 v/v mixture of toluene and ethyl acetate as eluant, and there was thus obtained as an oil (1RS, 2RS)-1-(9-n-heptylsulphinylnonyl)-2-p-hydroxyphenyl-1,2,3,4- tetrahydronaphth-6-ol, the structure of which was confirmed by proton magnetic resonance and mass spectroscopy.

The process described above was repeated using the appropriate alkylthioalkyl-naphthalene or indane derivative in Example 8 as starting material, and there were thus obtained the compounds described in the following tables:

TABLE 1

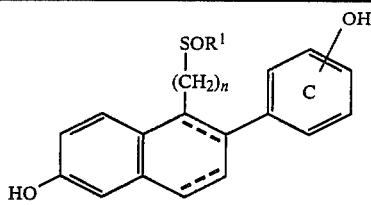

| n | $R^1$ | Optional Double Bonds | Position of OH in Ring C | Substituent in Ring C |
|---|---|---|---|---|
| 9 | n-heptyl | absent+ | 4- | — |
| 9 | n-heptyl | present | 4- | — |
| 10 | n-hexyl | absent | 4- | — |
| 10 | n-hexyl | present | 4- | — |
| 10 | n-hexyl | absent | 4- | 2-methyl |
| 10 | n-hexyl | absent | 4- | 2-ethyl |
| 10 | n-hexyl | absent | 4- | 3-methyl |
| 10 | n-hexyl | absent | 4- | 2,5-dimethyl |
| 10 | n-hexyl | absent | 3- | — |
| 11 | 4-chlorophenyl | absent | 4- | — |
| 11 | 4-chlorophenyl | present | 4- | — |

Note to TABLE 1
+All tetrahydronaphthalenes apart from the one marked + are (1RS,2RS)—isomers. The one marked + is a (1RS,2SR)—isomer.

TABLE 2

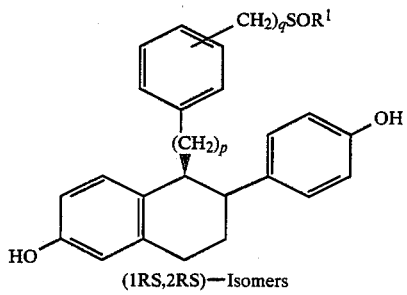

(1RS,2RS)—Isomers

| p | q | $R^1$ | Position of $(CH_2)_qSOR^1$ |
|---|---|---|---|
| 3 | 2 | n-octyl | 4- |
| 3 | 3 | n-heptyl | 4- |
| 4 | 1 | n-heptyl | 4- |
| 4 | 2 | n-hexyl | 4- |
| 4 | 2 | 4,4,5,5,5-pentafluoropentyl | 4- |
| 4 | 2 | 4,4,4-trifluorobutyl | 4- |
| 4 | 2 | benzyl | 4- |
| 4 | 2 | 4-methylbenzyl | 4- |
| 4 | 2 | 3,4-dichlorobenzyl | 4- |
| 4 | 2 | 4-chlorobenzyl | 4- |
| 4 | 2 | 4-phenylbenzyl | 4- |
| 4 | 2 | 4-methylthiobenzyl | 4- |
| 4 | 2 | 4-trifluoromethylbenzyl | 4- |
| 4 | 2 | 4-cyanobenzyl | 4- |
| 4 | 2 | phenethyl | 4- |
| 4 | 2 | 2-(4-chlorophenyl)ethyl | 4- |
| 4 | 2 | 2-(4-fluorophenyl)ethyl | 4- |
| 4 | 2 | n-hexyl | 3- |
| 4 | 3 | n-pentyl | 4- |
| 4 | 3 | 4-chlorobenzyl | 4- |
| 4 | 3 | n-hexyl | 3- |
| 5 | 1 | n-hexyl | 4- |
| 5 | 2 | 4,4,5,5,5-pentafluoropentyl | 4- |
| 5 | 2 | 4-chlorobenzyl | 4- |
| 5 | 2 | n-hexyl | 3- |
| 5 | 3 | n-pentyl | 4- |
| 5 | 3 | 4-chlorobenzyl | 3- |
| 6 | 2 | 4-chlorobenzyl | 4- |

TABLE 3

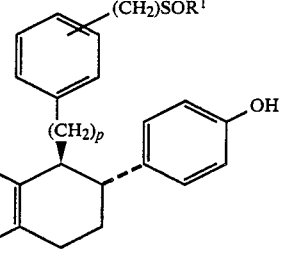

(1RS,2SR)—Isomers

| p | q | R¹ | Position of (CH₂)qSOR¹ |
|---|---|---|---|
| 4 | 2 | n-hexyl | 4- |
| 4 | 2 | 4,4,5,5,5-pentafluoropentyl | 4- |
| 4 | 2 | benzyl | 4- |
| 4 | 2 | 3,4-dichlorobenzyl | 4- |
| 4 | 2 | 4-trifluoromethylbenzyl | 4- |
| 4 | 2 | n-hexyl | 3- |

TABLE 4

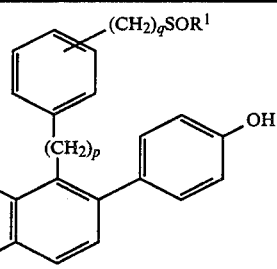

| p | q | R¹ | Position of (CH₂)qSOR¹ |
|---|---|---|---|
| 3 | 2 | n-octyl | 4- |
| 3 | 2 | n-octyl | 3- |
| 3 | 3 | n-heptyl | 4- |
| 4 | 3 | n-pentyl | 4- |
| 5 | 2 | n-hexyl | 4- |
| 5 | 2 | 4,4,5,5,5-pentafluoropentyl | 4- |
| 5 | 2 | 4-chlorobenzyl | 4- |
| 5 | 2 | n-hexyl | 3- |
| 5 | 3 | n-pentyl | 4- |
| 6 | 2 | 4-chlorobenzyl | 4- |

TABLE 5

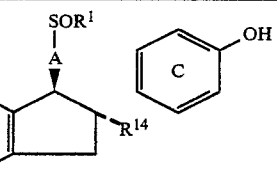

| A | R¹ | R¹⁴ | Substituted in Ring C |
|---|---|---|---|
| —(CH₂)₁₀— | n-hexyl | H | — |
| —(CH₂)₁₁— | n-hexyl | H | — |
| —(CH₂)₁₁— | n-pentyl | H | — |
| —(CH₂)₁₁— | n-butyl | H | — |
| —(CH₂)₄—C₆H₄—4-(CH₂)₂— | n-hexyl | H | — |
| —(CH₂)₄—C₆H₄—4-(CH₂)₂— | n-heptyl | methyl | — |
| —(CH₂)₄—C₆H₄—4-(CH₂)₂— | n-hexyl | methyl | — |
| —(CH₂)₄—C₆H₄—4-(CH₂)₂— | n-pentyl | methyl | — |
| —(CH₂)₄—C₆H₄—4-(CH₂)₃— | n-hexyl | methyl | — |
| —(CH₂)₄—C₆H₄—4-(CH₂)₃— | n-pentyl | methyl | — |
| —(CH₂)₄—C₆H₄—4-(CH₂)₂— | n-hexyl | ethyl | — |
| —(CH₂)₄—C₆H₄—4-(CH₂)₂— | n-pentyl | ethyl | — |
| —(CH₂)₄—C₆H₄—4-(CH₂)₃— | n-pentyl | ethyl | — |
| —(CH₂)₁₀— | n-hexyl* | H | 2,3,5,6-tetrafluoro |

TABLE 6

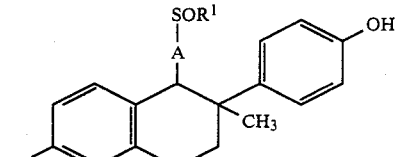

| A | R¹ |
|---|---|
| —(CH₂)₁₀— | n-hexyl |
| —(CH₂)₁₀— | n-pentyl |
| —(CH₂)₄—C₆H₄—4-(CH₂)— | n-hexyl |
| —(CH₂)₄—C₆H₄—4-(CH₂)₂— | n-hexyl* |
| —(CH₂)₄—C₆H₄—4-(CH₂)₂ | p-hydroxybenzyl |
| —(CH₂)₄—C₆H₄—4-(CH₂)₂— | 4,4,5,5,5-pentafluoropentyl |
| —(CH₂)₆—O—(CH₂)₃— | n-pentyl |

*Note to TABLE 6
The compound marked * is the (1RS,2SR) isomer.

TABLE 7

| A | R¹ | Optional Double Bonds |
|---|---|---|
| —(CH₂)₄—C₆H₄—4-CH(CH₃CH₂— | n-hexyl | absent |
| —(CH₂)₄—C₆H₄—4-C(CH₃)₂CH₂— | n-hexyl | absent |
| —(CH₂)₃—(2,6-naphthylene)-CH₂— | n-heptyl | present |
| —(CH₂)₄—(2,6-naphthylene)-CH₂— | n-pentyl | absent |

EXAMPLE 10 m-Chloroperbenzoic acid (0.15 g.) was added to a stirred solution of (1RS, 2RS)-1-(9-n-heptylthiononyl)-6-methoxy-2-p-methoxyphenyl-1,2,3,4-tetrahydronaphthalene (Example 7; 0.2 g.) in chloroform (50 ml.) and the mixture was stirred for 2 hours and then poured into saturated aqueous sodium bicarbonate solution (30 ml.). The organic layer was separated, washed with water, dried and evaporated to dryness and the residue was purified by chromatography on a silica gel column using a 10:1 v/v mixture of toluene and ethyl acetate as eluant. A solution of boron tribromide (2.1 g.) in methylene chloride (3 ml.) was added to a stirred solution of the (1RS, 2RS)-1-(9-n-heptylsulphonylnonyl)-6-methoxy-2-p-methoxyphenyl-1,2,3,4-tetrahydronaphthalene thus obtained (0.19 g.) in methylene chloride (10 ml.) which was cooled to −70° C. under an atmosphere of argon, and the mixture was allowed to warm up to 0°

C., stirred at that temperature for 3 hours and then poured onto ice (20 g.). The mixture was extracted three times with methylene chloride (15 ml. each time) and the combined extracts were washed with water, dried and evaporated to dryness. The residue was purified by chromatography on a silica gel column using a 5:1 v/v mixture of toluene and ethyl acetate as eluant, and there was thus obtained (1RS, 2RS)-1-(9-n-heptyl-sulphonylnonyl)-2-p-hydroxyphenyl- 1,2,3,4-tetrahydronaphth-6-ol, the structure of which was confirmed by proton magnetic resonance and mass spectroscopy.

The process described above was repeated using the appropriate alkylthioalkyl-methoxynaphthalene or indane derivative obtained as an intermediate for a compound described in Example 8 as starting material, and there were thus obtained the compounds described in the following tables:

TABLE I

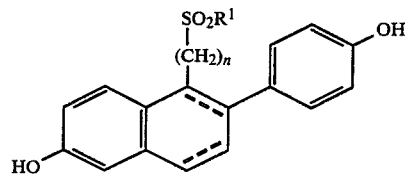

| n | $R^1$ | Optional Double Bonds |
|---|---|---|
| 9 | n-heptyl | present |
| 11 | 4-chlorophenyl | absent |

TABLE 2

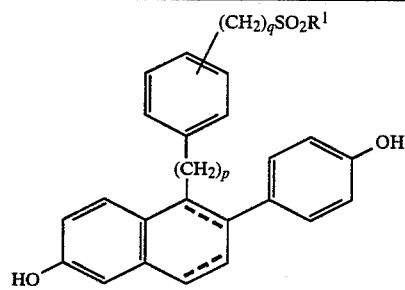

| p | q | $R^1$ | Position of $(CH_2)_qSO_2R^1$ | Optional Double Bonds |
|---|---|---|---|---|
| 4 | 2 | n-hexyl | 4- | absent |
| 4 | 2 | 4-chlorobenyzl | 4- | absent |
| 4 | 2 | 4-trifluoromethylbenzyl | 4- | absent |
| 4 | 3 | n-pentyl | 4- | absent |
| 4 | 3 | 4-chlorobenzyl | 4- | absent |
| 4 | 3 | n-hexyl | 3- | absent |
| 5 | 3 | 4-chlorobenzyl | 3- | absent |
| 5 | 2 | 4-chlorobenzyl | 4- | present |

TABLE 3

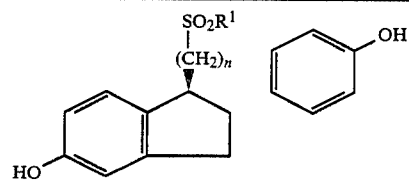

| n | $R^1$ |
|---|---|
| 10 | n-hexyl |
| 11 | n-pentyl |
| 11 | n-butyl |

TABLE 4

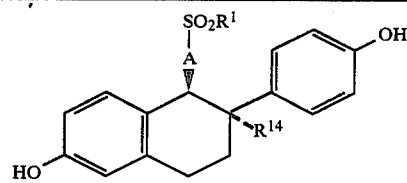

| A | $R^1$ | $R^{14}$ |
|---|---|---|
| —$(CH_2)_4$—2,6-naphthylene-$CH_2$— | n-pentyl | H |
| —$(CH_2)_6$—O—$(CH_2)_3$— | n-pentyl | methyl |

EXAMPLE 11

A solution of isobutyl chloroformate (0.117 g.) in methylene chloride (5 ml.) was added to a stirred solution of 9-(6-hydroxy-2-p-hydroxyphenylbenzo[b]thien-3-yl)nonanoic acid (0.1 g.) and N-methylmorpholine (0.145 g.) in methylene chloride (10 ml.) which was cooled to −30° C., and the mixture was allowed to warm up to laboratory temperature. A solution of n-heptylamine (0.098 g.) in methylene chloride (5 ml.) was added and the mixture was stirred at laboratory temperature for 1 hour and then evaporated to dryness. The residue was dissolved in methanol (5 ml.), aqueous 40% sodium hydroxide solution (2 ml.) was added and the mixture was stirred for 5 minutes and then acidified with concentrated aqueous hydrochloric acid and extracted three times with diethyl ether (20 ml. each time). The combined extracts were washed with water, dried and evaporated to dryness and the residue was purified by chromatography on a silica gel column using a 100:3 v/v mixture of methylene chloride and methanol as eluant. There was thus obtained as an oil N-n-heptyl-9-(6-hydroxy-2-p-hydroxyphenylbenzo[b]thien-3-yl)nonanamide, the structure of which was confirmed by proton magnetic resonance and mass spectroscopy.

The process described above was repeated using N-n-heptyl-N-methylamine in place of n-heptylamine. There was thus obtained N-n-heptyl-9-(6-hydroxy-2-p-hydroxyphenylbenzo[b]thien-3-yl)-N-methylnonanamide.

The nonanoic acid used as starting material was obtained as follows:

A mixture of monomethyl azelate (7.88 g.) and thionyl chloride (100 ml.) was heated under reflux for 1 hour, the excess of thionyl chloride was removed by evaporation and the residue was dissolved in ethylene dichloride (400 ml.). The solution was stirred vigorously and 6-p-chlorophenacyloxy-2-(4-p-chlorophenacyloxyphenyl)benzo[b]thiophene (21.3 g.; prepared as described in U.S. Pat. No. 4,133,814) was added, followed by the portionwise addition of aluminium chloride (36.4 g.). The mixture was stirred at laboratory temperature for 40 minutes, methanol (100 ml.) was added and the mixture was evaporated to dryness. The residue was purified by chromatography on a silica gel column using a 10:1 v/v mixture of toluene and ethyl acetate as eluant. There was thus obtained methyl 9-oxo-9-[6-p-chlorophenacyloxy-2-(4-p-chlorophenacyloxyphenyl)benzo[b]thien-3-yl]nonanoate, m.p. 132°–136° C.

Zinc dust (26.2 g.) was added to a solution of the above ester (14.7 g.) in acetic acid (200 ml.) and the mixture was stirred and heated at 60° C. for 30 minutes. Water (400 ml.) and diethyl ether (200 ml.) were added and the organic layer was separated, dried and evaporated to dryness. The residue was dissolved in methanol (200 ml.), aqueous 40% sodium hydroxide solution (100 ml.) was added and the mixture was stirred at laboratory temperature for 30 minutes. Water (200 ml.) was added and the mixture was washed twice with diethyl ether (75 ml. each time). The aqueous solution was acidified with concentrated aqueous hydrochloric acid and the mixture was extracted three times with diethyl ether (150 ml. each time). The combined extracts were washed with water, dried and evaporated to dryness and the residue was stirred with methylene chloride. The mixture was filtered and there was thus obtained as solid product 9-oxo-9-(6-hydroxy-2-p-hydroxyphenylbenzo[b]thien-3-yl)nonanoic acid, m.p. 154°–158° C.

A solution of the above acid (4.12 g.) in hydrazine hydrate (10 ml.) was heated under reflux for 30 minutes, powdered potassium hydroxide (15 g.) was added and the mixture was heated at 185° C. (bath temperature) for 4 hours and then cooled. Water (50 ml.) was added and the solution was acidified with concentrated aqueous hydrochloric acid and extracted three times with diethyl ether (75 ml. each time). The combined extracts were washed with water, dried and evaporated to dryness and the residue was purified by chromatography on a silica gel column using a 25:1 v/v mixture of methylene chloride and methanol as eluant. There was thus obtained as an oil 9-(6-hydroxy-2-p-hydroxyphenylbenzo[b]thien-3-yl)nonanoic acid.

EXAMPLE 12

The process described in Example 11 was repeated except that 9-(2,3-dihydro-6-hydroxy-2-p-hydroxyphenylbenzo[b]thien-3-yl)nonanoic acid and either heptylamine or N-methylheptylamine were used as starting materials. There were thus separately obtained as oils N-n-heptyl- and N-n-heptyl-N-methyl-9-(2,3-dihydro-6-hydroxy-2-p-hydroxyphenylbenzo[b]thien-3yl)nonanamide, the structures of which were confirmed by proton magnetic resonance and mass spectroscopy.

The starting material was obtained as follows:

A mixture of 9-(6-hydroxy-2-p-hydroxyphenylbenzo[b]thien-3-yl)nonanoic acid (Example 11; 2.86 g.), triethylsilane (3.3 g.) and trifluoroacetic acid (15 ml.) was stirred and heated under reflux for 18 hours and then evaporated to dryness under reduced pressure. The residue was purified by chromatography on a silica gel column which had been impregnated with silver nitrate, using a 10:1 v/v mixture of methylene chloride and methanol as eluant. There was thus obtained 9-(2,3-dihydro-6-hydroxy-2-p-hydroxyphenylbenzo[b]thien-3-yl)nonanoic acid which was shown by proton magnetic resonance spectroscopy to be 93% trans-isomer and 7% cis-isomer at the 2 and 3 positions.

EXAMPLE 13

A solution of isobutyl chloroformate (0.1 g.) in methylene chloride (5 ml.) was added to a stirred solution of 12,13-di-p-methoxyphenylpentadec-12-enoic acid (0.28 g. of a mixture of geometrical isomers contaminated with some corresponding 13-enoic acid) and N-methylmorpholine (0.12 g.) in methylene chloride (10 ml.) which was cooled to −30° C. under an atmosphere of argon, and the mixture was allowed to warm up to laboratory temperature. A solution of n-pentylamine (0.5 ml.) in methylene chloride (5 ml.) was added and the mixture was stirred at laboratory temperature for 1 hour. Aqueous 2 N-hydrochloric acid (30 ml.) was added and the mixture was extracted three times with diethyl ether (30 ml. each time). The combined extracts were washed with water, dried and evaporated to dryness. A solution of boron tribromide (0.5 g.) in methylene chloride (3 ml.) was added to a stirred solution of the predominantly 12,13-di-p-methoxyphenyl-N-pentylpentadec-12-enamide thus obtained (0.32 g.) in methylene chloride (10 ml.) which was cooled to −30° C. under an atmosphere of argon, and the mixture was allowed to warm up to laboratory temperature and was stirred at that temperature for 30 minutes. Water (5 ml.) was added and the mixture was extracted three times with methylene chloride (20 ml. each time). The combined extracts were washed with water, dried and evaporated to dryness and the residue was purified by chromatography on a silica gel column using a 10:3 v/v mixture of toluene and ethyl acetate as eluant. There was thus obtained as an oil 12,13-di-p-hydroxyphenyl-N-pentylpentadec-12-enamide, which was shown by proton magnetic resonance spectroscopy to be a 9:1 by weight mixture of trans- and cis-isomers.

The pentadecenoic acid used as starting material was obtained as follows:

n-Butyl-lithium (3.55 ml. of a 1.55 molar solution in hexane) was added to a stirred solution of diisopropylamine (0.55 g.) in tetrahydrofuran (10 ml.) which was cooled to 0° C. under an atmosphere of argon, and the mixture was stirred at 0° C. for 15 minutes and then cooled to −70° C. A solution of 4,4'-dimethoxydesoxybenzoin (1.28 g.) in tetrahydrofuran (25 ml.), followed by a solution of t-butyl 11-iodoundecanoate (2.03 g.) in tetrahydrofuran (5 ml.), were added and the mixture was allowed to warm up to laboratory temperature and was then heated under reflux for 6 hours and cooled. Water (20 ml.) was added and the mixture was extracted three times with diethyl ether (30 ml. each time). The combined extracts were washed with water, dried and evaporated to dryness and the residue was purified by chromatography on a silica gel column using a 2:1 v/v mixture of petroleum ether (b.p. 40°–60° C.) and diethyl ether as eluant.

A Grignard reagent prepared from a stirred suspension of magnesium turnings (0.16 g.) in diethyl ether (5 ml.) and a solution of ethyl iodide (0.94 g.) in diethyl ether (10 ml.) was added to a stirred solution of the t-butyl 12,13-di-p-methoxyphenyl-13-oxotridecanoate thus obtained (1.51 g.) in diethyl ether (20 ml.) and the mixture was stirred at laboratory temperature for 3 hours. Saturated aqueous ammonium chloride solution (15 ml.) was added and the mixture was extracted three times with diethyl ether (30 ml. each time). The combined extracts were washed with water, dried and evaporated to dryness and the residue was purified by chromatography on a silica gel column using a 2:1 v/v mixture of petroleum ether (b.p. 40°-60° C.) and diethyl ether as eluant.

A mixture of the t-butyl 13-hydroxy-12,13-di-p-methoxyphenylpentadecanoate thus obtained (1.0 g.) and p-toluenesulphonic acid (0.01 g.) was stirred and heated at 120° C. under vacuum (50 mm.Hg) for 1 hour and was then purified by chromatography on a silica gel column using a 1:1 v/v mixture of petroleum ether (b.p. 40°-60° C.) and diethyl ether as eluant. There was thus obtained a mixture of cis- and trans-isomers of 12,13-di-p-methoxyphenylpentadec-12- and -13- enoic acid.

EXAMPLE 14

The process described in Example 13 was repeated using the appropriate di-p-methoxyphenylalkenoic acid and the appropriate amine as starting materials. There were thus obtained as oils the compounds described in the following table, which were mixture of cis- and trans-isomers and the structures of all of which were confirmed by proton magnetic resonance and mass spectroscopy:

| $R^6$ | n | $R^1$ | $R^2$ |
|---|---|---|---|
| methyl | 10 | n-pentyl | H |
| ethyl | 8 | n-hexyl | H |
| ethyl | 8 | n-hexyl | methyl |
| ethyl | 8 | n-heptyl | H |
| ethyl | 8 | n-heptyl | methyl |
| ethyl | 6 | n-heptyl | methyl |
| ethyl | 6 | n-octyl | H |
| ethyl | 6 | n-octyl | methyl |
| ethyl | 6 | n-nonyl | H |
| ethyl | 6 | n-decyl | H |

The alkenoic acids used as starting materials were prepared by a similar process to that described in Example 13 using the appropriate t-butyl omegaiodoalkanoate in the process of the third paragraph and methyl or ethyl iodide to form the Grignard reagent for the process of the fourth paragraph.

EXAMPLE 15

N-methylmorpholine (0.105 ml.) and isobutyl chloroformate (0.126 ml.) were successively added to a stirred solution of (13RS, 14SR)-13,14-di-p-methoxyphenyl-hexadec-10-enoic acid (0.361 g.) in methylene chloride (15 ml.) which was cooled to −10° C., and the mixture was stirred at that temperature for 30 minutes. n-Butylamine (0.126 ml.) was added and the mixture was stirred for 30 minutes and then evaporated to dryness. The residue was purified by chromatography on a silica gel column using a 7:3 v/v mixture of toluene and ethyl acetate as eluant.

A solution of the N-butyl-(13RS,14SR)-13,14-di-p-methoxyphenylhexadec-10-enamide thus obtained (0.322 g.) in ethyl acetate (15 ml.) was shaken with hydrogen in the presence of a 5% palladium-on-charcoal catalyst (0.03 g.) until one equivalent of hydrogen had been absorbed, the mixture was filtered and the filtrate was evaporated to dryness. A solution of boron tribromide (0.5 ml.) in methylene chloride (1 ml.) was added dropwise to a stirred solution of the residue (0.311 g.) in methylene chloride (5 ml.) which was cooled to −78° C. under an atmosphere of argon, and the mixture was allowed to warm up to −20° C., stirred at that temperature for 4 hours and then poured into ice-water (25 ml.). The mixture was extracted twice with ethyl acetate (10 ml. each time). The combined extracts were washed with saturated aqueous sodium chloride solution (5 ml.), dried and evaporated to dryness and the residue was purified by chromatography on a silica gel column using an 11:9 v/v mixture of toluene and ethyl acetate as eluant. There was thus obtained as an oil N-n-butyl-(13RS,14SR)-13,14-di-p-hydroxyphenylhexadecanamide, the structure of which was confirmed by proton magnetic resonance and mass spectroscopy as follows:

Mass Spectrocopy: M+ =496.

| Proton Magnetic Resonance Spectrum (400 MHz in CDCl$_3$) | | | |
|---|---|---|---|
| Shift (δ) | Type of Peak | No of protons | Assignment |
| 7.0 | Doublet | 4 | )Aromatic |
| 6.82 | Doublet | 4 | )Protons |
| 5.63 | Multiplet | 1 | —NH— |
| 3.29 | Quartet | 2 | —CH$_2$—N— |
| 2.52 | Double triplet | 1 | —CH— |
| 2.4 | Double triplet | 1 | |
| 2.2 | Triplet | 2 | —CH$_2$—CO— |
| 1.68 | Quintet | 2 | —CH$_2$—(CH$_2$CO—) |
| 1.49 | Quintet | 2 | —CH$_2$—(CH$_2$NH—) |
| 1–1.4 | Multiplet | 25 | Other aliphatic protons |
| 0.51 | Triplet | 3 | 16-CH$_3$ |

Thin layer chromatography (silica gel plates using a 1:1 v/v mixture of ethyl acetate and toluene).

R$_F$=0.48

The process described above was repeated except that N-methyl-N-n-butylamine was used as starting material in place of n-butylamine. There was thus obtained as an oil N-n-butyl-(13RS,14SR)-13,14-di-p-hydroxyphenyl-N-methylhexadecanamide.

The hexadecenoic acid used as starting material was obtained as follows:

Di-isobutylaluminium hydride (3.45 ml of a 1.4 molar solution in toluene) was added dropwise to a stirred solution of methyl 3,4-di-p-methoxyphenylhexanoate (1.59 g.; prepared as described in Journal of Medicinal Chemistry, 1980, 23, 1002) in toluene (25 ml.) which was cooled to −60° C. under an atmosphere of argon, and the mixture was stirred for 25 minutes. Methanol (5 ml.) was added, the mixture was allowed to warm up to laboratory temperature and aqueous N-hydrochloric acid (25 ml.) was added. The organic layer was separated, the aqueous layer was extracted with toluene (25 ml.) and the combined organic solutions were dried and evaporated to dryness. The residue was purified by chromatography on a silica gel column using a 19:1 v/v mixture of toluene and ethyl acetate as eluant.

A solution of the (3RS,4SR)-3,4-di-p-methoxyphenylhexanal thus obtained (0.312 g.) in a mixture of dimethyl sulphoxide (1 ml.) and toluene (2 ml.) was added dropwise under an atmosphere of argon to a stirred solution of (9-carboxynonyl)triphenylphosphonium bromide (1.539 g.; prepared from 10-bromodecanoic acid and triphenylphosphine in acetonitrile solution, and freshly dried and finely powdered immediately before use) in a mixture of dimethyl sulphoxide (3 ml) and toluene (1 ml.), to which methanesulphinyl sodium (2.7 ml. of a 2- molar solution in dimethyl sul-phoxide) had been added 15 minutes previously. The mixture was stirred for 25 minutes, aqueous N-hydrochloric acid (25 ml.) was added and the mixture was extracted twice with ethyl acetate (10 ml. each time). The combined extracts were evaporated to dryness under reduced pressure, the residue was dissolved in ethyl acetate (2 ml.) and the solution was washed with water (5 ml.), dried and evaporated to dryness. The residue was purified by chromatography on a silica gel column using a 1:1 v/v mixture of toluene and ethyl acetate as eluant. There was thus obtained as an oil (13RS,14SR)-13,14-di-p-methoxyphenylhexadec-10-enoic acid.

EXAMPLE 16

The process decribed in Example 15 was repeated using the appropriate amine and the appropriate di-p-methoxyphenylakenoic acid as starting materials. There were thus obtained the compounds described in the following table. Except where otherwise stated all compounds were oils the structures of which were confirmed by proton magnetic resonance and mass spectroscopy. Also except where otherwise stated $R^{14}$ is hydrogen and the stereochemistry at the two carbon atoms bearing the —$(CH_2)_n$—$CONR^1R^2$ and the —$R^6$ substituents is (SR), (RS) respectively.

| $R^6$ | n | $R^1$ | $R^2$ | Notes |
|---|---|---|---|---|
| ethyl | 5 | n-hexyl | H | |
| ethyl | 6 | n-hexyl | H | |
| ethyl | 6 | n-heptyl | H | |
| ethyl | 6 | n-nonyl | H | |
| ethyl | 6 | n-decyl | H | |
| methyl | 6 | n-octyl | H | |
| ethyl | 6 | n-octyl | H | the two optical isomers have $[\alpha]_D^{20}$ −8.6° and $[\alpha]_D^{20}$ + 8.7° (both c, 0.7% in $CHCl_3$) |
| ethyl | 6 | n-octyl | H | |
| n-propyl | 6 | n-octyl | H | m.p. 74–76° C. |
| methyl | 6 | n-octyl | H | $R^{11}$ = methyl |
| methyl | 6 | n-octyl | H | 3-F substituent in ring B; m.p. 41–44° C. |
| methyl | 6 | n-octyl | H | 3-F substituent in ring C. |
| ethyl | 6 | n-octyl | H | 3-F substituent in ring C. |
| ethyl | 7 | n-heptyl | H | |
| ethyl | 7 | n-octyl | H | |
| ethyl | 7 | n-octyl | methyl | |
| ethyl | 7 | n-nonyl | H | |
| ethyl | 8 | n-pentyl | H | |
| ethyl | 8 | n-heptyl | H | |
| ethyl | 9 | n-butyl | H | |
| ethyl | 9 | n-butyl | methyl | |
| ethyl | 9 | n-octyl | H | |
| ethyl | 10 | n-butyl | H | |
| ethyl | 10 | n-butyl | methyl | |
| methyl | 10 | n-butyl | methyl | 2,3,5,6-tetra-F substituent in ring B |

The di-p-methoxyphenylalkenoic acids used as starting materials were all prepared from the appropriate 2,3-di-p-methoxyphenylalkanal and the appropriate (omega-carboxyalkyl)triphenylphosphonium bromide by a similar process to that described in the last part of Example 15. The various alkanals were themselves obtained as follows:

(2RS, 3SR)-2,3-di-p-methoxyphenylhexanal ($R^6$=n-propyl)

The Grignard reagent prepared from propyl bromide (8.17 ml.) and magnesium turnings (2.19 g.) in diethyl ether (18 ml.) was added dropwise to a stirred solution of trans-2,3-di-p-methoxyphenylacrylonitrile (7.8 g.), and cuprous iodide (0.57 g.) in tetrahydrofuran (300 ml.) which was cooled to −20° C. under an atmosphere of argon, and the mixture was stirred at that temperature for 150 minutes and then poured onto a stirred mixture of ice and aqueous 2 N-hydrochloric acid (300 ml.). The organic solvent was removed by evaporation and the aqueous residue was extracted twice with ethyl acetate (150 ml. each time). The combined extracts were washed with saturated aqueous ammonium chloride solution (100 ml.), dried and evaporated to dryness and the residue was crystallised from 96% aqueous ethanol. There was thus obtained (2RS,3SR)-2,3-di-p-methoxyphenylhexanonitrile, m.p. 122°–123° C.

Diisobutylaluminium hydride (4.5 ml. of a 1.2 molar solution in toluene) was added dropwise to a stirred solution of the above compound (1.39 g.) in toluene (18 ml.) which was cooled to −78° C. under an atmosphere of argon, and the mixture was stirred at that temperature for 1 hour. Methanol (2 ml.) was added, the mixture was allowed to warm up slowly to laboratory temperature, ethyl acetate (75 ml.) was added and the mixture was stirred and then filtered. The filtrate was evaporated to dryness, the residue was dissolved in toluene and the solution was filtered through silica. The filtrate was evaporated to dryness and there was thus obtained as residue (2RS,3SR)-2,3-di-p-methoxyphenylhexanal, m.p. 84°–86° C.

(2RS,3SR)-3-(3-fluoro-4-methoxyphenyl)-2-p-methoxyphenylpentanal ($R^6$=ethyl, 3-F in ring C)

A mixture of p-methoxyphenylacetonitrile (18.4 g.) and 3-fluoro-4-methoxybenzaldehyde (18.5 g.) was added dropwise to a stirred solution of sodium (5.5 g.) in ethanol (300 ml.) which was heated under reflux, and the mixture was stirred and heated under reflux for 30 minutes, cooled and filtered. The trans-3-(3-fluoro-4-methoxyphenyl)-2-p-methoxyphenylacrylonitrile (m.p 148°–149° C.) thus obtained was reacted with ethyl magnesium bromide, and the product of that reaction was reacted with diisobutylaluminium hydride, by a similar process to that described in the preceding paragraph, and there were thus successively obtained (2RS,3SR)-3-(3-fluoro-4-methoxyphenyl)-2-p-methoxyphenylpentanonitrile, m.p. 149°–150° C., and (2RS,3SR)-3-(3-fluoro-4-methoxyphenyl)-2-p-methoxyphenylpentanal, m.p. 108°–110° C.

(2RS,3SR)-3-(3-fluoro-4-methoxyphenyl)-2-p-methoxyphenylbutanal ($R^6$=methyl,3-F in ring C)

This was obtained by a similar process to that described in the preceding paragraph, using methyl magnesium bromide in place of ethyl magnesium bromide.

(2RS,3SR)-2-(3-fluoro-4-methoxyphenyl)-3-p-methoxyphenylbutanal ($R^6$=methyl,3-F in ring B)

A mixture of methanol (60 ml.), sodium borohydride (1.3 g.) and 3-fluoro-4-methoxybenzaldehyde (10 g.) was stirred at laboratory temperature for 10 minutes and then evaporated to dryness. The residue was partitioned between water (20 ml.) and ethyl acetate (50 ml.) and the ethyl acetate layer was washed with water, dried and evaporated to dryness. The residual 3-fluoro-4-methoxybenzyl alcohol (9.5 g.) was purified by chromatography on a silica gel column using a 1:1 v/v mixture of toluene and ethyl acetate as eluant and was then rapidly stirred with concentrated aqueous hydrochloric acid for 15 minutes. The organic layer consisting of 3-fluoro-4-methoxybenzyl chloride (9.5 g.) was separated, dried over calcium chloride and heated under reflux with acetone (30 ml.), sodium iodide (0.6g.) and sodium cyanide (4.41 g.) for 20 hours. The mixture was filtered and the filtrate was evaporated to dryness.

The 3-fluoro-4-methoxyphenylacetonitrile thus obtained was reacted with anisaldehyde by a similar process to that described in the preceding paragraphs, and the trans- 2-(3-fluoro-4-methoxyphenyl)-3-p-methoxyphenylacrylonitrile (m.p. 146°–148° C.) thus obtained was reacted with methyl magnesium iodide, and the product of that reaction was reacted with diisobutylaluminium hydride, as described above. There were thus successively obtained (2RS,3SR)-2-(3-fluoro-4-methoxyphenyl)-3-p-methoxyphenylbutanonitrile, m.p. 132°–134° C. and (2RS,3SR)-2-(3-fluoro-4-methoxyphenyl)-3-p-methoxyphenylbutanal, m.p. 86°–92° C.

(2RS,3SR)-2,3-di-p-methoxyphenylbutanal (R$^6$-methyl)

The process described in the preceding paragraphs was repeated using trans-2,3-di-p-methoxyphenylacrylonitrile and methyl magnesium iodide as starting materials. There were thus successively obtained (2RS,3SR)-2,3-di-p-methoxyphenylbutanonitrile, m.p. 130°–132° C., and (2RS,3SR)-2,3-di-p-methoxyphenylbutanal, m.p. 125°–127° C.

2,3-di-p-methoxyphenyl-3-methylbutanal (R$^6$=R$^{14}$=methyl)

A solution of 4,4'-dimethoxydesoxybenzoin (2.56 g.) in tetrahydrofuran (30 ml.) was added dropwise during 5 minutes to a stirred suspension of potassium hydride (5 ml. of a 23.6% by weight suspension in mineral oil) in tetrahydrofuran (20 ml.) which was maintained under an atmosphere of argon, and the mixture was stirred for a further 5 minutes. Methyl iodide (1.5 ml.) was added during 5 minutes, the mixture was stirred for a further 15 minutes and water (3 ml.) was added. The organic solvents were removed by evaporation and the residue was partitioned between water (50 ml.) and ethyl acetate (50 ml.). The layers were separated, the aqueous layer was extracted with ethyl acetate (50 ml.) and the combined ethyl acetate solutions were washed with water, dried and evaporated to dryness. The residue was purified by chromatography on a silica gel column using a 9:1 v/v mixture of toluene and ethyl acetate as eluant, and there was thus obtained as an oil 4,4'-dimethoxy-, -dimethyldesoxybenzoin.

n-Butyl-lithium (7.2 ml. of a 1.39 molar solution in hexane) was added dropwise to a stirred suspension of methyltriphenylphosphonium bromide (4.98 g.) in tetrahydrofuran (20 ml.) which was maintained under an atmosphere of argon, and the mixture was stirred for 30 minutes. A solution of the above desoxybenzoin (2.48 g.) in tetrahydrofuran (10 ml.) was added dropwise during 5 minutes and the mixture was stirred for 15 hours and then filtered. The filtrate was evaporated to dryness and a solution of the residue in ethyl acetate (10 ml.) was chromatographed on a silica gel column using toluene as eluant. There was thus obtained as an oil 2,3-di-p-methoxyphenyl-3-methylbut-1-ene.

A molar solution of borane in tetrahydrofuran (23 ml.) was added dropwise to a stirred solution of the above compound (1.99 g.) in tetrahydrofuran (16 ml.) which was maintained under an atmosphere of argon and the mixture was stirred for 1 hour. Aqueous N-sodium hydroxide solution (24 ml.) was carefully added, and hydrogen peroxide (10.2 ml., 110 volumes) was then added and the mixture was stirred for 1 hour. Water (50 ml.) was added and the mixture was extracted twice with diethyl ether (50 ml. each time). The combined extracts were dried and evaporated to dryness and there was thus obtained as residue 2,3-di-p-methoxyphenyl-3-methylbutan-1-ol, m.p. 121° C.

A mixture of the above butanol (0.6 g.), methylene chloride (20 ml.) and pyridinium chlorochromate (0.6 g.) was stirred for 150 minutes, diluted with diethyl ether (20 ml.) and filtered. The filtrate was evaporated to dryness and the residue was purified by chromatography on a silica gel column using a 19:1 v/v mixture of toluene and ethyl acetate as eluant. There was thus obtained as an oil 2,3-di-p-methoxyphenyl-3-methylbutanal.

(2RS,3SR)-2,3-di-p-methoxyphenylpentanal and (+)-(2S,3R)-2,3-di-p-methoxyphenylpentanal (R$^6$=ethyl)

Both the racemate and the (+)- isomer were obtained by the oxidation with pyridinium chlorochromate as described in the paragraph above, of the corresponding pentanols, both of which are described in the Australian Journal of Chemistry, 1970, 23, 1605.

EXAMPLE 17

The process described in Example 15 was repeated using 3-p-[(6RS,7SR)-6,7-di-p-methoxyphenylnonyl]-phenylpropionic acid and n-butylamine as starting materials. There was thus obtained as an oil N-n-butyl-3-p-[(6RS,7SR)-6,7-di-p-hydroxyphenylnonyl]phenylpropionamide, the structure of which was confirmed by proton magnetic resonance and mass spectroscopy.

The phenylpropionic acid used as starting material was obtained as follows:

A solution of (2RS,3SR)-2,3-di-p-methoxyphenylpentanal (Example 16; 1.0 g.) in tetrahydrofuran (20 ml.) was added to a stirred suspension of [2-(1,3-dioxan-2-yl)ethyl]triphenylphosphonium bromide (1.5 g.) in tetrahydrofuran (30 ml.), to which n-butyl-lithium (2 ml. of a 1.5 molar solution in hexane) had been added, at −20° C., and the mixture was stirred for 10 minutes. Water (50 ml.) was added and the mixture was extracted three times with diethyl ether (75 ml. each time). The combined extracts were dried and evaporated to dryness and the residue was purified by chromatography on a silica gel column using a 7:3 v/v mixture of petroleum ether (b.p. 40°–60° C.) and diethyl ether as eluant. A solution of the 2-[(4RS,5SR)-4,5-di-p-methoxyphenylhept-2-enyl]-1,3-dioxan thus obtained (1.2 g.) in ethyl acetate (100 ml.) was stirred under an atmosphere of hydrogen for 16 hours in the presence of a 10% palladium-on-charcoal catalyst (0.15 g.), the mixture was filtered and the filtrate was evaporated to dryness. A solution of the residue (1.12 g.) in a mixture of tetrahydrofuran (5 ml.) and dimethylformamide (25 ml.) was added to a 4-molar solution of chromic chloride in aqueous hydrochloric acid (25 ml.) and the mixture was heated under reflux for 4 hours, then kept at laboratory temperature for 16 hours and extracted three times with diethyl ether (50 ml. each time). The combined extracts were washed with water and then with saturated aqueous sodium chloride solution, dried and evaporated to dryness. The residue was purified by chromatography on a silica gel column using a 4:1 v/v mixture of petroleum ether (b.p. 40°14 60° C.) and diethyl ether as eluant. There was thus obtained (5RS,6SR)-5,6-di-p-methoxyphenyloctanal.

n-Butyl-lithium (1.14 ml. of a 1.5 molar solution in hexane) was added dropwise to a stirred solution of diisopropylamine (0.18 g.) in tetrahydrofuran (3 ml.) which was cooled to −70° C. under an atmosphere of argon, and the mixture was stirred for 15 minutes at that temperature. A solution of ethyl p-diethoxyphosphonylmethylcinnamate (0.58 g.) in tetrahydrofuran was added and the mixture was stirred for 10 minutes at −70° C. A solution of the above octanal (0.3 g.) in tetrahydrofuran (3 ml.) was then added and the mixture was allowed to warm up to laboratory temperature, stirred at that temperature for 16 hours and then poured into aqueous 2 N-hydrochloric acid. The mixture was extracted three times with diethyl ether (20 ml. each time) and the combined extracts were washed with water, dried and evaporated to dryness. The residue was purified by chromatography on a silica gel column using a 4:1 v/v mixture of petroleum ether (b.p. 40°–60° C.) and diethyl ether as eluant.

A solution of the ethyl p-[(6RS,7SR)-6,7-di-p-methoxyphenylnon-1-enyl]cinnamate thus obtained (0.39 g.) in ethyl acetate (20 ml.) was stirred under an atmosphere of hydrogen in the presence of a 10% palladium-on-charcoal catalyst (0.1 g.) for 2 hours, the mixture was filtered and the filtrate was evaporated to dryness. Aqueous 40% sodium hydroxide solution (1 ml.) was added to a solution of the residue in methanol (20 ml.) and the mixture was stirred at laboratory temperature for 16 hours and then evaporated to dryness. The residue was acidified with aqueous 2 N-hydrochloric acid and the mixture was extracted three times with ethyl acetate (30 ml. each time). The combined extracts were washed with water, dried and evaporated to dryness and there was thus obtained as residue 3-p-[(6RS,7SR)-6,7-di-p-methoxyphenylnonyl]phenylpropionic acid.

EXAMPLE 18

The process described in Example 15 was repeated using 3-p-[(6RS, 7SR)-6,7-di-p-methoxyphenyloctyl]phenylpropionic acid and 1H,1H-heptafluorobutylamine as starting materials. There was thus obtained as an oil N-(1H,1H-heptafluorobutyl)-3-p-[(6RS, 7SR)-6,7-di-p-hydroxyphenyloctyl]phenylpropionamide, the structure of which was confirmed by proton magnetic resonance and mass spectroscopy.

The phenylpropionic acid used as starting material was obtained from (2RS, 3SR)-2,3-di-p-methoxyphenylbutanal (Example 16) by a similar process to that decribed in the second part of Example 17.

EXAMPLE 19

A mixture of 12,13-di-p-methoxyphenylpentadecanoic acid (0.2 g.) and thionyl chloride (5 ml.) was heated under reflux for 10 minutes, the excess of thionyl chloride was removed by evaporation and the residue was dissolved in methylene chloride (10 ml.). The solution was added to a stirred solution of n-pentylamine (1 ml.) in methylene chloride (5 ml.) which was cooled to 0° C., and the mixture was allowed to warm up to laboratory temperature and was then poured into aqueous 2 N-hydrochloric acid. The mixture was extracted three times with diethyl ether (30 ml. each time) and the combined extracts were washed with water, dried and evaporated to dryness. The residue was purified by chromatography on a silica gel column using diethyl ether as eluant. The residue was dissolved in methylene chloride and treated with boron tribromide by a similar process to that described in Example 15. There was thus obtained as an oil (12RS,13SR)-12,13-di-p-hydroxyphenyl-N-n-pentylpentadecanamide, the structure of which was confirmed by proton magnetic resonance and mass spectroscopy.

The pentadecanoic acid used as starting material was obtained by the hydrogenation in ethyl acetate solution in the presence of acetic acid and a 20% palladium-on-charcoal catayst of the mixture of cis-and trans-isomers of 12,13-di-p-methoxyphenylpentadec-12-and -13-enoic acids described in Example 13.

EXAMPLE 20

The process described in Example 1 was repeated using 2-{p-[5-(6-methoxy-2-p-methoxyphenylnaphth-1-yl)pentyl]phenyl}cyclopropanecarboxylic acid and N-methyl-1H,1H-heptafluorobutylamine as starting materials. There was thus obtained as an oil N-(1H,1H-heptafluorobutyl)-2-{p-[5-(6-hydroxy-2-p-hydroxyphenylnaphth-1-yl)pentyl]phenyl}-N-methylcyclopropanecarboxamide, the structure of which was confirmed by proton magnetic resonance and mass spectroscopy.

The cyclopropanecarboxylic acid used as starting material was obtained as follows:

A solution of ethyl 3-p-[5-(6-methoxy-2-p-methoxyphenylnaphth-1-yl)pentyl]phenylpropionate (0.4 g.; Example 3) in tetrahydrofuran (10 ml.) was added to a stirred solution of n-butyllithium (0.6 ml. of a 1.5 molar solution of hexane) and diisopropylamine (0.13 g.) in tetrahydrofuran at −65° C. under an atmosphere of argon, and the mixture was stirred at −65° C. for 10 minutes. A solution of phenylselenyl bromide (0.22 g.) in tetrahydrofuran (8 ml.) was added and the mixture was allowed to warm up to 0° C. and stirred at that temperture for 1 hour. Aqueous 2 N-hydrochloric acid (20 ml.) was added and the mixture was extracted 3 times with diethyl ether (30 ml. each time). The combined extracts were washed with water, dried and evaporated to dryness and the residue was purified by chromatography on a silica gel column using toluene as eluant. Pyridine (0.24 ml.) and 30% w/v aqueous hydrogen peroxide solution (0.042 ml.) were successively added to a solution of the product in methylene chloride (20 ml.) and the mixture was stirred for 15 minutes. The organic layer was separated, washed with aqueous N-hydrochloric acid, dried and evaporated to dryness.

A solution of trimethylsulphoxonium iodide (1.2 g.) in dimethyl sulphoxide (10 ml.) was added to a stirred suspension of sodium hydride (0.24 g. of a 50% dispersion in mineral oil) in dimethyl sulphoxide (5 ml.), and 0.32 ml. of the mixture was added to a stirred solution of the ethyl 3-p-[5-(6-methoxy-2-p-methoxyphenylnaphth-1-yl)pentyl]phenylprop-trans-2-enoate (0.05 g.) thus obtained in dimethyl sulphoxide (1 ml.) under an atmosphere of argon. The mixture was stirred at laboratory temperature for 48 hours, water (20 ml.) was added and the mixture was extracted 3 times with diethyl ether (30 ml. each time). The combined extracts were washed with water, dried and evaporated to dryness and the residue was purified by chromatography on a silica gel column using a 19:1 v/v mixture of toluene and diethyl ether as eluant. The ethyl cyclopropanecarboxylate thus obtained was hydrolysed to the acid with aqueous potassium hydroxide solution and there was thus obtained the desired cyclopropanecarboxylic acid.

EXAMPLE 21

Water (20 ml.) and 40% aqueous tetrabutylammonium hydroxide solution (0.25 ml.) were successively added to a solution of 1,8-dibromooctane (19.9 g.) and hexanethiol (3.5 g.) in toluene (20 ml.) and the mixture was vigorously stirred at laboratory temperature for 2 hours. The layers were separated, the aqueous layer was extracted twice with toluene (10 ml. each time) and the combined toluene solutions were washed with water, dried and evaporated to dryness. The residue was purified by chromatography on a silica gel column using petroleum ether (b.p. 40°–60° C.) as eluant. A Grignard reagent was prepared from the 8-hexylthiooctyl bromide thus obtained (0.94 g.) and magnesium turnings (0.07 g.) in tetrahydrofuran (5 ml.) at 0° C. under an atmosphere of argon, and a solution of dilithium copper tetrachloride in tetrahydrofuran (0.65 ml., prepared as described in the Chemical and Pharmaceutical Bulletin, 1980, 28, 606) was added dropwise. A solution of 6-(dimethyl-t-butylsilyloxy)-2-p-(dimethyl-t-butylsilyloxy)phenyl-3,4-dihydro-1-(2-p-toluenesulphonyloxyethyl)naphthalene (0.2 g.) in tetrahydrofuran (10 ml.) was added and the mixture was stirred at 0° C. for 2 hours and then at laboratory temperature for 18 hours. Saturated aqueous potassium sodium tartrate solution (20 ml.) was added, the mixture was filtered and the filtrate was extracted three times with diethyl ether (20 ml. each time). The combined extracts were washed with water, dried and evaporated to dryness and the residue was purified by chromatography on a silica gel column using a 9:1 v/v mixture of petroleum ether (b.p. 40°–60° C.) and diethyl ether as eluant. A molar solution of tetrabutylammonium fluoride in tetrahydrofuran (0.5 ml.) was added to a solution of the product (0.15 g.) in tetrahydrofuran (5 ml.) and the mixture was stirred at laboratory temperature for 30 minutes and then evaporated to dryness. The residue was purified by chromatography on a silica gel column using a 3:2 v/v mixture of petroleum ether (b.p. 40°–60° C.) and diethyl ether as eluant. There was thus obtained as an oil 1-(10-hexylthiodecyl)-3,4-dihydro-2-p-hydroxyphenyl-naphth-6-ol, the structure of which was confirmed by proton magnetic resonance and mass spectroscopy.

The above compound was oxidised with sodium metaperiodate by a similar process to that decribed in Example 9, and there was thus obtained 1-(10-hexylsulphinyldecyl)-3,4-dihydro-2-p-hydroxyphenylnaphth-6-ol.

The 6-(dimethyl-t-butylsilyloxy)-2-p-(dimethyl-t-butylsilyloxy)phenyl-3,4-dihydro-1-(2-p-toluenesulphonyloxyethyl)naphthalene used as starting material was obtained as follows:

3,4-Dihydro-6-methoxy-2-p-methoxyphenylnaphthalen-1(2H)-one (11 g.) was added portionwise to pyridine hydrochloride [prepared from pyridine (46 ml.) and concentrated (11.3 N) aqueous hydrochloric acid (50 ml.) which had been heated at 210° C.] at 170° C., and the mixture was heated at 210° C. for 30 minutes, cooled and filtered. The solid product was washed with water, dried and washed with petroleum ether (b.p. 40°–60° C.). A solution of dimethyl-t-butylsilyl chloride (10.6 g.) in tetrahydrofuran (100 ml.) was added dropwise to a stirred solution of the solid product (8.5 g.) and imidazole (9.5 g.) in tetrahydrofuran (150 ml.) and the mixture was stirred at laboratory temperature for 3 hours and then filtered. The filtrate was evaporated to dryness and the residue was purified by chromatography on a silica gel column using a 1:1 v/v mixture of toluene and petroleum ether (b.p. 40°–60° C.) as eluant. There was thus obtained 6-(dimethyl-t-butylsilyloxy)-2-p-(dimethyl-t-butylsilyloxy)phenyl-3,4-dihydronaphthalen-1(2H)-one, m.p. 75°–77° C.

A stirred mixture of the above compound (12.5 g.) ethyl bromoacetate (13 g.), zinc (8.7 g.), benzene (300 ml.) and one crystal of iodine was heated under reflux under an atmosphere of argon for 30 minutes, cooled to laboratory temperature and saturated aqueous ammonium chloride solution (100 ml.) was added. The mixture was filtered and the organic layer of the filtrate was separated, dried and evaporated to dryness. p-Toluenesulphonic acid (0.01 g.) was added to a solution of the residue in toluene (200 ml.) and the mixture was heated under reflux in a Dean and Stark water-separating apparatus for 30 minutes. The solution was evaporated to dryness and the residue was purified by chromatography on a silica gel column using a 9:1 v/v mixture of petroleum ether (b.p. 40°–60° C.) and diethyl ether as eluant. There was thus obtained ethyl 2-[3,4-dihydro-6-(dimethyl-t-butylsilyoxy)-2-p-(dimethyl-t-butylsilyloxy) phenylnaphth-1-yl]acetate, m.p. 73°–75° C.

A solution of the above compound (0.8 g.) in tetrahydrofuran (15 ml.) was added under an atmosphere of argon to a stirred suspension of lithium aluminium hydride (0.1 g.) in tetrahydrofuran (10 ml.) and the mixture was stirred at laboratory temperature for 1 hour. A saturated aqueous potassium sodium tartrate solution (10 ml.) was added and the mixture was extracted 3 times with diethyl ether (30 ml. each time). The combined extracts were washed with water, dried and evaporated to dryness. Pyridine (0.52 ml.) was added to a stirred solution of the ethanol thus obtained (0.65 g.) and p-toluenesulphonyl chloride (0.73 g.) in methylene chloride (20 ml.) which was cooled to 5° C., and the mixture was allowed to warm up to laboratory temperature and was stirred at that temperature for 2 hours and then evaporated to dryness. The residue was purified by chromatography on a silica gel column using a 9:1 v/v mixture of petroleum ether (b.p. 40°–60° C. ) and diethyl ether as eluant. There was thus obtained the desired p-toluenesulphonyloxyethyl starting material.

EXAMPLE 22

A solution of 1-(10-bromodecyl)-5-methoxy-2-p-methoxyphenylind-1-ene (0.24 g.) in dimethylformamide (1 ml.) was added to a stirred solution of hexanethiol (0.07 g.) and sodium hydride (0.029 g. of a 50% dispersion in mineral oil from which the oil had been washed with petroleum ether) in dimethylformamide which had been stirred at laboratory temperature under an atmosphere of argon for 15 minutes, and the mixture was heated at 60° C. for 2 hours, cooled and water (5 ml.) was added. The mixture was extracted 3 times with ethyl acetate (5 ml. each time) and the combined extracts were washed with water, dried and evaporated to dryness. The residue was purified by chromatography on a silica gel column using a 1:1 v/v mixture of toluene and petroleum ether (b.p. 60°–80° C.) as eluant. The methoxy groups were removed by treatment with boron tribromide in a similar manner to that decribed in Example 7, and the residue was purified by chromatography on a silica gel column using a 9:1 v/v mixture of toluene and ethyl acetate as eluant. There was thus obtained as an oil 1-(10-hexylthiodecyl)-2-p-hydroxyphenylind-1-en-5-ol, the structure of which was confirmed by proton magnetic resonance and mass spectroscopy.

The 1-(10-bromodecyl)-5-methoxy-2-p-methoxyphenylind-1-ene used as starting material was obtained as follows:

p-Toluenesulphonic acid (0.005 g.) was added to a solution of 1-[10-(dimethyl-t-butylsilyloxy)decyl]-5-methoxy-2-p-methoxyphenylindan-1-ol (6 g.; Example 4) in toluene (200 ml.), and the mixture was evaporated to dryness. The residue was purified by chromatography on a silica gel column using toluene as eluant. A molar solution of tetrabutylammonium fluoride in tetrahydrofuran ( 5.8 ml.) was added to a stirred solution of the product obtained (0.6 g.) in tetrahydrofuran (10 ml.) and the mixture was stirred at laboratory temperature for 2 hours and then evaporated to dryness. The residue was purified by chromatography on a silica gel column using a 4:1 v/v mixture of toluene and ethyl acetate as eluant. Carbon tetrabromide (0.22 g.) was added to a stirred solution of the 1-(10-hydroxydecyl)-5-methoxy-2-p-methoxyphenylind-1-ene thus obtained (0.3 g.) in methylene chloride (5 ml.), the mixture was cooled to 10° C. and a solution of triphenylphosphine (0.17 g.) in methylene chloride (2 ml.) was added. The mixture was stirred at laboratory temperature for 2 hours and then evaporated to dryness, and the residue was purified by chromatography on a silica gel column using toluene as eluant. There was thus obtained 1-(10-bromodecyl)-5-methoxy-2-p-methoxyphenylind-1-ene.

EXAMPLE 23

The process described in Example 22 was repeated except that 1-(10-bromodecyl)-5-methoxy-2-p-methoxyphenyl-3-methylind-1-ene was used as starting material. There was thus obtained as an oil 1-(10-hexylthiodecyl)-2-p-hydroxyphenyl-3-methylind-1-en-5-ol, the structure of which was confirmed by proton magnetic resonance and mass spectroscopy.

The starting material was obtained as follows:

A solution of p-methoxyphenylacetic acid (0.83 g.) in tetrahydrofuran (5 ml.) was added to a stirred solution of n-butyllithium (6.8 ml. of a 1.6 molar solution in hexane) and diisopropylamine (1.5 ml.) in tetrahydrofuran (2 ml.) which was cooled to −30° C. under an atmosphere of argon, and the mixture was allowed to warm up to laboratory temperature and was stirred at that temperature for 1 hour. A solution of 1-m-methoxyphenylethyl chloride (1.13 g; described in the Journal of Medicinal Chemistry, 1981, 24, 1192) in tetrahydrofuran (2 ml.) was added and the mixture was stirred at 35° C. for 3 hours. Water (20 ml.) was added and the mixture was acidified with concentrated aqueous hydrochloric acid and extracted three times with diethyl ether (30 ml. each time). The combined extracts were washed with water, dried and evaporated to dryness and the residue was purified by chromatography on a silica gel column using a 19:1 v/v mixture of methylene chloride and methanol as eluant. An excess of thionyl chloride was added to a solution of the 2,3-bis-(p-methoxyphenyl)butyric acid thus obtained (0.95 g.) in toluene (10 ml.) and the mixture was heated at 100° C. for 2 hours and then evaporated to dryness. Stannic chloride (0.4 ml.) was added dropwise to a stirred solution of the acid chloride thus obtained in methylene chloride (10 ml.) which was cooled to 0° C. under an atmosphere of argon, and the mixture was stirred at 0° C. for 2 hours and then poured into ice-water (20 ml.). The mixture was extracted 3 times with methylene chloride (10 ml. each time) and the combined extracts were washed with water, dried and evaporated to dryness. The residue was purified by chromatography on a silica gel column using a 9:1 v/v mixture of toluene and ethyl acetate as eluant and there was thus obtained 5-methoxy-2-p-methoxyphenyl-3-methylindan-1-one, m.p. 106°–108° C.

This indanone was reacted with the Grignard reagent from 10-(dimethyl-t-butylsilyloxy)decylbromide by a similar process to that described in Example 4, and the product obtained was converted to the desired 10-bromodecylind-1-ene by a similar process to that described in Example 22.

EXAMPLE 24

Aqueous N-sodium hydroxide solution (0.62 ml.) and acetic anhydride (0.084 g.) were successively added to a stirred solution of 11-(6-hydroxy-2-p-hydroxyphenylnaphth-1-yl)-N-n-pentylundecanamide (0.1 g., Example 2) in acetone (30 ml.) which was cooled to 0° C., and the mixture was stirred at that temperature for 1 hour and then poured onto aqueous 2 N-hydrochloric acid (20 ml.). The mixture was extracted three times with diethyl ether (30 ml. each time) and the combined extracts were washed with water, dried and evaporated to dryness. The residue was purified by chromatography on a silica gel column using a 100:1 v/v mixture of methylene chloride and methanol as eluant, and the solid product obtained was crystallised from a mixture of toluene and petroleum ether (b.p. 60°–80° C.). There was thus obtained 11-(6-acetoxy-2-p-acetoxyphenylnaphth-1-yl)-N-n-pentylundecanamide, m.p. 101°–103° C.

The process described above was repeated using benzoyl chloride in place of acetic anhydride, and there was thus obtained 11-(6-benzoyloxy-2-p-benzoyloxyphenylnaphth-1-yl)-N-n-pentylundecanamide, m.p. 120°–122° C. after crystallisation from the same solvent mixture.

The process described above was repeated using N-(1H,1H-heptafluorobutyl)-3-p-[5-(6-hydroxy-2-p-hydroxyphenylnaphth-1-yl)pentyl]phenyl-N-methylpropionamide (Example 3) and acetic anhydride or pivalic anhydride as starting materials. The products were purified by chromatography on a silica gel column using a 19:1 v/v mixture of toluene and ethyl acetate as eluant, and there were thus respectively obtained 3-p-[5-(6-acetoxy-2-p-acetoxyphenylnaphth-1-yl)pentyl]phenyl-N-1H,1H-heptafluorobutyl-N-methylpropionamide and the corresponding (6-pivalyloxy-2-p-pivalyloxyphenylnaphth-1-yl)-derivative.

What we claim is:

1. A phenol derivative of the formula:

$$NU-A-X-R^1$$

where NU is a bis-phenolic nucleus of the general formula

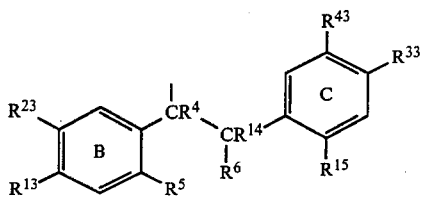

wherein one of $R^{13}$ and $R^{23}$, and one of $R^{33}$ and $R^{43}$, has the formula $R^3O$-, wherein each $R^3$, which may be the same or different, is hydrogen or alkyl, cyaloalkyl, alkanoyl, alkoxycarbonyl, carboxyalkanoyl, or aroyl each of up to 10 carbon atoms, and wherein the other of $R^{13}$ and $R^{23}$, and the other of $R^{33}$ and $R^{43}$, is hydrogen:

wherein $R^4$ and $R^{14}$, which may be the same or different, each is hydrogen or alkyl of up to 5 carbon atoms, or $R^4$ and $R^{14}$ are joined together so that $CR^4$-$CR^{14}$ is an olefinic double bond;

wherein $R^5$ and $R^6$ together form a direct link or —CH$_2$—, —CH(CH$_3$)—, —CH$_2$CH$_2$—, —(CH$_2$)$_3$— or —CH=CH—, and $R^{15}$ is hydrogen;

and wherein the aromatic rings B and C each is unsubstituted or substituted with one or more halogen or methyl or ethyl substituents;

where A is straight- or branched-chain alkylene, alkenylene or alkynylene each of from 4 to 12 carbon atoms;

or A has the formula:

—A$^1$—Y$^3$—A$^{21}$— wherein A$^1$ is alkylene or alkenylene and A$^{21}$ is a direct link or alkylene, alkenylene or cycloalkylene, such that A$^1$ and A$^{21}$ together have a total of 2 to 10 carbon atoms, and Y$^3$ is phenylene or naphthylene which is unsubstituted or substituted with one or more halogen or methyl or ethyl substituents;

wherein R$^1$ is alkyl, alkenyl, cycloalkyl, halogenoalkyl, each of up to 10 carbon atoms, phenyl, chlorophenyl, o-ethylphenyl, p-cyanophenyl, p-hydroxyphenyl, p-methoxyphenyl, alkyl of 1 to 3 carbon atoms which bears a phenyl, tolyl, halogenophenyl or trifluoromethylphenyl substituent, α-methylbenzyl, 3,4-dichlorobenzyl, p-cyanobenzyl or p-methylthiobenzyl; and wherein X is —S—, —SO— or —SO$_2$—;

or a pharmaceutically acceptable salt of a compound wherein R$^3$ is carboxyalkanoyl.

2. A phenol derivative as claimed in claim 1 wherein R$^{15}$, R$^{23}$ and R$^{43}$ are all hydrogen; wherein R$^{13}$ and R$^{33}$ both have the formula R$^3$O- wherein R$^3$ is hydrogen or alkanoyl or alkoxycarbonyl each of up to 5 carbon atoms; wherein either R$^4$ is hydrogen and R$^{14}$ is hydrogen, methyl or ethyl, or R$^4$ and R$^{14}$ are joined together so that CR$^4$—CR$^{14}$ is an olefinic double bond;

wherein R$^5$ and R$^6$ together form —CH$_2$—, —CH(CH$_3$)—, —CH$_2$CH$_2$—, or —CH=CH—; wherein the aromatic rings B and C either bear no further substituent or bear one or more fluoro, methyl or ethyl substitutents;

wherein the group —A— is a straight chain alkylene group of the formula

—(CH$_2$)$_n$— wherein n is an integer of from 4 to 12 or the group A is a group of the formula:

—A$^1$—Y$^3$—A$^{21}$— wherein A$^1$ is straight-chain alkylene of 2 to 9 carbon atoms, —Y$^3$— is meta- or para-phenylene and A$^{21}$ is a direct link, methylene, ethylene, or trimethylene;

wherein X is —S—, —SO— or —SO$_2$—; and wherein R$^1$ is n-butyl, isobutyl, t-butyl, n-pentyl, isopentyl, t-pentyl, 2,2-dimethylpropyl, 1-methylbutyl, 2-methylbutyl, n-hexyl, 1,1-dimethylbutyl, 1,3-dimethylbutyl, n-heptyl, n-decyl, cyclopentyl, cyclohexyl, phenyl, o-ethylphenyl, p-chlorophenyl, m-chlorophenyl, p-cyanophenyl, p-hydroxyphenyl, p-methoxyphenyl, benzyl, α-methylbenzyl, p-chlorobenzyl, p-methylbenzyl, 3,4-dichlorobenzyl, p-cyanobenzyl, p-methylthiobenzyl, p-trifluoromethylbenzyl, phenethyl, p-fluorophenethyl, p-chlorophenethyl, 1H, 1H, -heptafluorobutyl, 4,4,5,5,5-pentafluoropentyl or 1H, 1H, 2H, 2H, 3H, 3H-heptafluorohexyl.

3. A phenol derivative as claimed in claim 1 wherein the number of carbon atoms in the two groups A and R$^1$ adds up to 14 to 16 if neither R$^1$ nor A contains a phenyl or phenyl group, 17 or 19 if there is either a phenylene group in —A— or a phenyl group in R$^1$, and 19 to 21 if there are both a phenylene group in —A— and a phenyl group in R$^1$.

4. A phenol derivative as claimed in claim 1 wherein:
NU is 6-hydroxy-2-p-hydroxyphenylnaphth-1-yl and A is —(CH$_2$)$_{10}$—, —(CH$_2$)$_{11}$— or —(CH$_2$)$_5$—(1,4-phenylene)—(CH$_2$)$_2$—;

or NU is (1RS, 2RS)— or (1RS, 2SR)—1,2,3,4-tetrahydro-6-hydroxy-2-p-hydroxyphenylnaphthyl-1-yl, or NU is (1RS, 2RS)— or (1RS,2SR)- 1,2,3,4,-tetrahydro-6-hydroxy-2-p-hydroxyphenyl-2-methylnaphth-1-yl, and A is —(CH$_2$)$_{10}$—, —(CH$_2$)$_{10}$—, —(CH$_2$)$_{11}$— or —(CH$_2$)$_4$-(1-4-phenylene)-(CH$_2$)$_2$—;

or NU is (1RS, 2RS)-5-hydroxy-2-p-hydroxy-phenyl-indan-1-yl or (1RS, 2RS)-5-hydroxy-2-p-hydroxyphenyl-2-methylindan-1-yl and A is —(CH$_2$)$_{10}$—, —(CH$_2$)$_{11}$— or —(CH$_2$)$_4$—(1,4-phenylene)—(CH$_2$)$_2$—;

and wherein XR$^1$ is —SR$^1$, SOR$^1$ or —SO$_2$R$^1$ wherein R$^1$ is n-pentyl, n-hexyl, 4,4,5,5,5-pentafluoropentyl or 1H,1H,2H,2H,3H,3H-heptafluorohexyl.

5. A pharmaceutical composition having antiestrogenic activity comprising an effective amount of a phenol derivative, claimed in claim 1, together with a pharmaceutically acceptable diluent or carrier.

6. A composition as claimed in claim 5 which contains, in addition to the phenol derivative an effective amount of one or more antiandrogenic agents or antiprogestational agents.

7. A method for producing an antioestrogenic effect in a warm-blooded animal in need of such treatment, which comprises administering to said animal an effective amount of at least one phenol derivative as claimed in claim 1.

8. A phenol derivative as claimed in claim 1 wherein R$^{15}$, R$^{23}$ and R$^{43}$ are all hydrogen, wherein R$^{13}$ and R$^{33}$ both have the formula R$^3$O— wherein R$^3$ is hydrogen, wherein either R$^4$ is hydrogen and R$^{14}$ is hydrogen, methyl or ethyl, or $R^4$ and $R^{14}$ are joined together, wherein $R^5$ and $R^6$ together form —CH$_2$—, —CH$_2$CH$_2$—, —CH(CH$_3$)—, or —CH=CH—, wherein —A— is —(CH$_2$)$_n$—, wherein n is an integer from 4 to 12, or —A— is

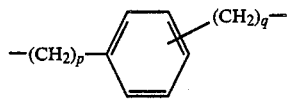

wherein p is an integer from 2 to 9, q is 0 to 3, and the —(CH$_2$)$_q$— group is in the meta- or para-position; wherein $R^1$ is alkyl or fluoroalkyl each of 4 to 10 carbon atoms, or phenyl or chlorophenyl, or alkyl of 1 to 3 carbon atoms which bears a phenyl, tolyl, halogenophenyl or trifluoromethylphenyl substituent, wherein X is —S—, —SO— or —SO$_2$—;

and wherein ring C is unsubstituted or substituted with one or two methyl substituents.

9. The compound:
(1RS, 2RS)-1-{4-[p-(2-n-hexylthioethyl)phenyl]butyl}-2-p-hydroxyphenyl-1,2,3,4-tetrahydronaphth-6-ol or the corresponding 4,4,5,5,5-pentafluoropentylthio derivative, or the corresponding hexylsulphinyl, hexylsulphonyl or pentafluoropentylsulphinyl derivative;

2-p-hydroxyphenyl-1-{5-[p-(3-n-hexylthioethyl)-p-pentyl]pentyl}naphth-6-ol or the corresponding hexylsulphinyl derivative;

(1RS, 2RS)-1-{4-[p-(2-hexylthioethyl)phenyl]butyl}-2-p-hydroxyphenyl-2-methyl-1,2,3,4-tetrahydronaphth-6-ol or the corresponding 4,4,5,5,5-pentafluoropentylthio derivative, or the corresponding hexylsulfinyl, hexylsulphonyl or pentafluoropentylsulphinyl derivative, or the corresponding (1RS, 2SR) isomer of either the hexylthio or hexylsulphinyl derivative.

* * * * *